US012797339B2

(12) United States Patent
Vasisht et al.

(10) Patent No.: US 12,797,339 B2
(45) **Date of Patent: *Nov. 17, 2026**

(54) PROCESS FOR PREPARING NANOFORMULATION FOR DELIVERY OF BERBAMINE

(71) Applicant: PANJAB UNIVERSITY, CHANDIGARH, Chandigarh (IN)

(72) Inventors: Karan Vasisht, Chandigarh (IN); Maninder Karan, Chandigarh (IN); Neetika Sharma, Chandigarh (IN); Indu Pal Kaur, Chandigarh (IN); Vikas Gautam, Chandigarh (IN); Simarjot Kaur Sandhu, Chandigarh (IN)

(73) Assignee: PANJAB UNIVERSITY, CHANDIGARH (IN)

( * ) Notice: Subject to any disclaimer, the term of this patent is extended or adjusted under 35 U.S.C. 154(b) by 463 days.

This patent is subject to a terminal disclaimer.

(21) Appl. No.: 18/276,227

(22) PCT Filed: Feb. 8, 2022

(86) PCT No.: PCT/IN2022/050103

§ 371 (c)(1),
(2) Date: Aug. 7, 2023

(87) PCT Pub. No.: WO2022/168123

PCT Pub. Date: Aug. 11, 2022

(65) Prior Publication Data

US 2024/0115512 A1 Apr. 11, 2024

(30) Foreign Application Priority Data

Feb. 8, 2021 (IN) ............................. 202111005302

(51) Int. Cl.

| | |
|---|---|
| *A61K 9/51* | (2006.01) |
| *A61K 31/473* | (2006.01) |
| *A61P 31/04* | (2006.01) |

(52) U.S. Cl.

CPC .......... *A61K 9/5123* (2013.01); *A61K 31/473* (2013.01); *A61P 31/04* (2018.01); *A61K 2800/41* (2013.01)

(58) Field of Classification Search

None

See application file for complete search history.

(56) References Cited

FOREIGN PATENT DOCUMENTS

| | | | |
|---|---|---|---|
| CN | 102078302 A | | 6/2011 |
| IN | 201811044487 A | | 8/2020 |
| WO | WO2020109989 A1 | * | 6/2020 |

OTHER PUBLICATIONS

"Preparation of berbamine loaded chitosan-agarose microspheres and in vitro release study" 2012.*

ChemBK 2015.*

Sankaranarayanan et al. "Ameliorating effect of berbamine on hepatic key enzymes of carbohydrate metabolism in high-fat diet and streptozotocin induced type 2 diabetic rats" Biomedicine & Pharmacotherapy vol. 103, Jul. 2018, pp. 539-545.

* cited by examiner

*Primary Examiner* — Danah Al-Awadi

(57) ABSTRACT

The present invention relates to a simple and convenient process for preparing solid lipid sustained release nanoparticles for berbamine delivery. The process involves preparation of nanoparticles by maintaining the pH of the aqueous or lipid phase so that high drug loading of 12-50% w/w with respect to the lipid matrix and high entrapment efficiency of more than 90% for berbamine in the solid lipid nanoparticles is achieved. The nanoformulation obtained by the process of the present invention has increased efficacy and exhibited any therapeutic property identical to free berbamine such as antiviral-cum-antibacterial agent for the treatment of microbial infections especially resistant *Acinetobacter* infections in treating diabetes and more specifically diabetes associated complications. Use may be extended to other diseases like COVID 19.

20 Claims, 24 Drawing Sheets

A

B

A

B

A. B.

a)

b)

*(contd....)* c)

d)

*(contd....)* e)

a)

b)

c)

a)

b)

(contd....)

c)

d)

a) Naïve; 40X b) Naïve; 100X c) Disease control; 40X d) Disease control; 100X e) Disease control; 100X

*(contd....)* f) Berbamine loaded SLNs gel; 40X g) Berbamine loaded SLNs gel; 100X h) Berbamine gel; 40X i) Berbamine gel; 100X j) Blank SLNs gel; 40X k) Blank SLNs gel; 100X

*(contd....)* l) Marketed standard; 40X m) Marketed standard; 100X

} epidermis ← granulation tissue ➡ bundles of collagen ⇒ Pus ☆ dermal papillae

★ Vacuoles ▲ dermal appendages △ Abscess cavity ■ muscle layer ● necrosis

PROCESS FOR PREPARING NANOFORMULATION FOR DELIVERY OF BERBAMINE

FIELD OF THE INVENTION

This invention relates to a process of preparation of solid lipid nanoparticles (SLNs) of berbamine or its derivative forms or its related compounds or bisbenzylisoquinoline alkaloids-enriched fraction from plant extract or combination thereof. Also, the invention relates to berbamine loaded solid lipid nanoparticles which provide a controlled release formulation of berbamine with high drug loading and increased efficacy. The invention also relates to the berbamine SLNs for efficient drug delivery, therefore, intended to be used for dermatological or cosmeceutical purposes; for treating diabetes and more specifically diabetes associated complications, in wound healing, as an antimicrobial or as an anti-infective for the treatment of microbial infections especially resistant to *Acinetobacter* infections.

BACKGROUND OF THE INVENTION

Berbamine is a naturally occurring bisbenzylisoquinoline alkaloid which is reported to be present in species of *Berberis, Mahonia, Cyclea, Thalictrum* and in *Pycnarrhena novoguineensis, Stephania cepharantha, Atherosperma moshatum.*

A number of pharmacological activities have been reported for this compound including antibacterial and antiviral activities, treatment of various types of cancers, cardiovascular diseases etc. However, no berbamine formulation has been marketed or clinically used and the same is indicated due to poor bioavailability and unstable nature of the compound (Parhi et al., 2016; DOI: 10.1038/s41598-017-05296-y).

CN102078302A discloses preparation of chitosan-agar nano particles, Method of preparation involves dissolving berbamine into chitosan acetum, dropwise adding sodium tripolyphoshate aqueous solution serving as a cross linking agent, centrifuging and freeze drying to obtain drug-loaded chitosan nano particles; and adding the chitosan nano particles into a hot agar aqueous solution, centrifuging and freeze drying to obtain the berbamine chitosan-agar nano particles.

The procedure for preparation of nanoparticles is very complicated and cumbersome and involves use of organic solvents.

Therefore, there is a need of an industrially viable process for preparing berbamine nanoparticles, preferably without using any organic solvents to ensure zero toxicity.

US 2011/0250239 discloses preparation of nanoemulsion of a water-soluble plant extract. Process for the preparation of a pharmaceutical and/or cosmetic composition comprises the steps: a) providing an aqueous component, b) providing a carrier comprising at least one lipophilic component, at least one surfactant and at least one alcohol, wherein the alcohol comprises preferably at least two carbon atoms, c) mixing the aqueous component of step a) with the carrier of step b), whereby a nanoemulsion is formed, d) adding an aqueous plant extract, in particular a water-soluble plant from *Mahonia aquifolium* to the mixture obtained in step c) prior to and/or after the formation of said nanoemulsion and e) optionally adding further additives and/or excipients to the mixture obtained in step d). f) the aqueous plant extract is added to the mixture obtained in step c) after formation of a nanoemulsion.

Nanoemulsion was prepared using organic solvents and moreover, they did not provide controlled release of the drug or (berbamine).

Therefore, there is a need of a process for preparing berbamine solid lipid nanoparticles which results in a controlled release of the molecules. Also, there is a requirement of a process in which no organic solvent is used and which is industrially viable and scalable.

WO 2017/208172 A1 relates to a composition for use as a medicament, in the form of a gel with characteristics of a reversible thermogel, based on one or more poloxamers, water and optionally excipients, and an effective amount of an active substance. Furthermore, this prior art relates to a process for the preparation of said composition and uses thereof.

It involves preparation of a thermoreversible gel of the plant actives which do not allow controlled release of the drug moreover, the method is expensive and also not industrially viable.

Therefore, there is a need of a process for preparing solid lipid nanoparticles of the molecule with an increase in water solubility, permeability and stability of the molecule resulting in higher bioavailability.

Parhi et al., 2016 (DOI: 10.1038/s41598-017-05296-y): Solid lipid nanoparticles are reported to be prepared by emulsification followed by sonication method which is not a control release method.

Sonication results in contamination with metal particles which could be harmful.

Therefore, there is a need of a process for preparing solid lipid nanoparticles with simple, easily scalable and industrially viable method which provides control release of the drug, moreover, it is simple, easily scalable and industrially viable.

Wu et al., 2015 (DOI: 10.1166/jbn.2015.2110) discloses preparation of polymeric nanoparticles using chitosan/sulfobutylether-β-cyclodextrin. containing docetaxel (DTX) and berbamine. These NPs were prepared using ionic gelation method and were characterised for their particle size, polydispersity, zeta potential, drug loading percentage and yield.

Ethanol was used in the preparation of the nanoparticles, which were prepared by a very lengthy and cumbersome method. Sulfobutylether-β-cyclodextrin is a costly component. Further low drug loading of only 0.33% is reported.

Therefore, there is a need of a process for preparing solid lipid nanoparticles by using simple, easily scalable and industrially amenable method. Also, there is a need for preparing nanoformulation with high drug loading and without using any organic solvent.

The various formulations disclosed in the prior arts involve a lengthy and cumbersome method with the use of organic solvent. Therefore, there is need for the simple and economic process for the preparation of berbamine loaded SLNs which gives better bioavailability and stability to berbamine.

OBJECTIVE OF THE INVENTION

Accordingly, it is an objective of the present invention to provide a simple, convenient, economical and industry friendly easily scalable process of preparing controlled release formulation of berbamine or its derivative or bisbenzylisoquinoline alkaloids-enriched fraction from berberis extract or their combination thereof using Generally Recognised as Safe (GRAS) components, which has improved bioavailability and stability.

It is another objective of the present invention to prepare lipid-based berbamine nanoformulation which can show enhanced penetration through biological membrane due to resemblance of lipid including phospholipid to biological membranes thereby achieving effective delivery to epidermal, dermal, and subcutaneous layers following topical application.

It is another object of the present invention to provide a controlled release formulation of berbamine leading to reduction in dose and frequency of administration.

It is another object of the present invention to provide solid lipid nanoparticle with high total drug content and drug loading.

It is another object of the present invention to provide the solid lipid nanoparticles prepared by the process in the form of a dispersion therefore can be used for efficient oral, parenteral, ocular, dental, buccal, intranasal, vaginal, rectal, otic, transdermal and topical delivery.

SUMMARY OF INVENTION

The present invention provides a process for preparation of solid lipid nanoparticles which address the aforesaid drawbacks of the prior arts. For example, the present invention provides preparation of solid lipid nanoparticles which are much more industrially viable than chitosan-agar nano particles. Moreover, process of preparation of solid lipid nanoparticles provides controlled release of the molecule. Further in the present invention, high drug loading of about 25% was achieved without using any organic solvent to ensure there is no toxicity. Solid lipid nanoparticles are prepared by hot high-pressure homogenisation method, which is simple, industrially viable and easily scalable. Also, the present invention involves preparation of solid lipid nanoparticles of the molecule with an increase in /OR enhanced water solubility, permeability and stability of the molecule resulting in higher bioavailability.

Accordingly, the present invention provides a process for preparing solid lipid nanoparticles of berbamine, the process comprising the steps of:

- i) preparing a lipid phase by melting one or more lipid selected from the group consisting of glycerides and fatty acids at a temperature at least equal to the melting point of said one or more lipid;
- ii) separately preparing an aqueous phase by admixing at least a surfactant, a co-surfactant and water followed by heating at a temperature at least equal to said melting point of said one or more lipid of step (i);
- iii) dissolving berbamine in an aqueous phase or in lipid phase, and maintaining the solution at pH 6-8.5;
- iv) adding the berbamine containing hot lipid phase of step (iii) to the aqueous phase of step (ii) or adding the berbamine containing aqueous phase of step (iii) to the lipid phase of step (i) and mixing at high speed of 5,000-20,000 rpm at the said pH for 5-30 min to obtain a primary coarse emulsion; and
- v) subjecting the primary coarse emulsion of step (iv) to two to six cycles of homogenization at 500 to 1200 bars to obtain solid lipid nanoparticles of berbamine.

In another aspect of the present invention there is provided Solid lipid nanoparticles of berbamine prepared by the process as described herein.

In yet another aspect, the formulation is used for treating diabetes and more specifically diabetes associated complications.

In yet another aspect, the formulation is used as a wound healer, as an antimicrobial, as an anti-inflammatory agent and for the treatment of microbial infections especially resistant to *Acinetobacter* infections.

Further, SLNs exhibit any therapeutic property identical to free berbamine.

BRIEF DESCRIPTION OF DRAWINGS

The accompanying drawings illustrate embodiments of the invention and, together with the description, serve to explain the invention. These drawings are offered by way of illustration and not by way of limitation.

DESCRIPTION OF THE INVENTION

Figure 1:
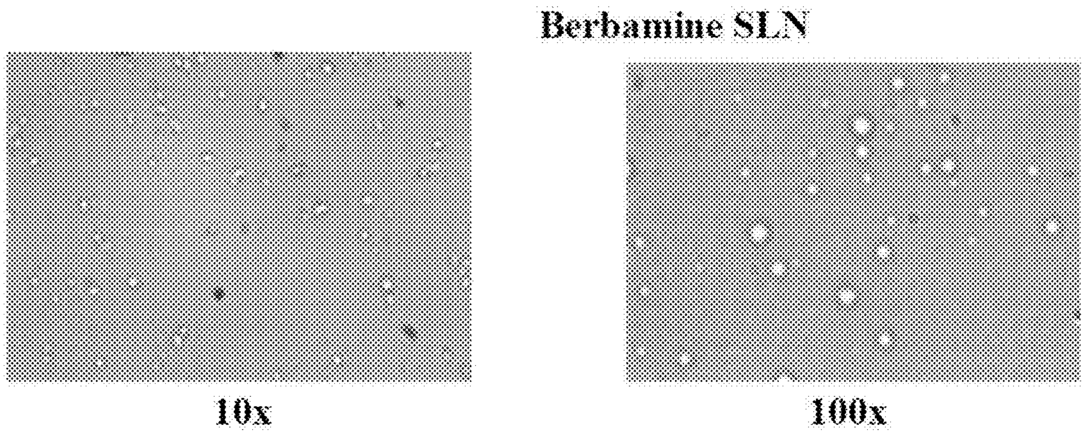
FIG. 1: illustrates optical microscope images of berbamine SLNs.

The invention will now be described in detail in connection with certain preferred and optional embodiments, so that various aspects thereof may be more fully understood and appreciated.

The following description with reference to the accompanying drawings is provided to assist in a comprehensive understanding of exemplary embodiments of the invention. It includes various specific details to assist in that understanding but these are to be regarded as merely exemplary. Accordingly, those of ordinary skill in the art will recognize that various changes and modifications of the embodiments described herein can be made without departing from the scope of the invention. In addition, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

As used herein, the "berbamine" refers to berbamine, berbamine analogues, berbamine complexes, berbamine derivatives including but not limiting to polymorphs, solvates, enantiomers, stereoisomer, salts, esters, amides, hydrates, bisbenzylisoquinoline alkaloids-enriched fraction from plant extract or any combination thereof.

The present invention relates to a process for preparing solid lipid nanoparticles of berbamine, the process comprising the steps of:

i) preparing a lipid phase by melting one or more lipid selected from the group consisting of glycerides and fatty acids at a temperature at least equal to the melting point of said one or more lipid;

ii) separately preparing an aqueous phase by admixing at least a surfactant, a co-surfactant and water followed by heating at a temperature at least equal to said melting point of said one or more lipid of step (i);

iii) dissolving berbamine in an aqueous phase or in lipid phase, and maintaining the solution at pH 6-8.5;

iv) adding the berbamine containing hot lipid phase of step (iii) to the aqueous phase of step (ii) or adding the berbamine containing aqueous phase of step (iii) to the lipid phase of step (i) and mixing at high speed of 5,000-20,000 rpm at the said pH for 5-30 min to obtain a primary coarse emulsion; and v) subjecting the primary coarse emulsion of step (iv) to two to six cycles of homogenization at 500 to 1200 bars to obtain solid lipid nanoparticles of berbamine.

In the process as described herein, the berbamine is amphiphilic in nature and thus can be dissolved in both lipid and aqueous phase. However, to obtain maximum solubility, the pH was kept around 7.5 to 8.5 when berbamine is dissolved in water phase and pH was kept around 6.0 to 7.0, when berbamine is dissolved in lipid phase.

In an embodiment, the present invention relates to a process for preparing solid lipid nanoparticles of berbamine, the process comprising the steps of:

i) preparing a lipid phase by melting one or more lipid selected from the group consisting of glycerides and fatty acids at a temperature at least equal to the melting point of said one or more lipid;

ii) separately preparing an aqueous phase by admixing at least one surfactant, co-surfactant and water followed by heating at a temperature at least equal to said melting point of said one or more lipid of step (i);

iii) dissolving berbamine in the aqueous phase, and maintaining the solution at pH 7.5-8.5; iv) adding the hot lipid mix from step (i) to the berbamine containing aqueous solution from step (iii) and mixing at high speed of 5,000-20,000 rpm at the said pH for 5-30 min to obtain a primary coarse emulsion; and v) subjecting the primary coarse emulsion of step (iv) to two to six cycles of homogenization at 500 to 1200 bars to obtain solid lipid nanoparticles of berbamine.

In another embodiment, the present invention relates to a process for preparing solid lipid nanoparticles of berbamine, wherein the process comprising the steps of:

i) preparing a lipid phase by melting one or more lipid selected from the group consisting of glycerides and fatty acids at a temperature at least equal to the melting point of said one or more lipid;

ii) separately preparing an aqueous phase by admixing at least one surfactant, co-surfactant and water followed by heating at a temperature at least equal to said melting point of said one or more lipid of step (i);

iii) dissolving berbamine in the lipid phase, and maintaining the solution or dispersion at pH 6-7;

iv) adding the berbamine containing hot lipid phase from step (iii) to the aqueous phase from step (ii) and mixing at high speed of 5,000-20,000 rpm at the said pH for 5-30 min to obtain a primary coarse emulsion; and v) subjecting the primary coarse emulsion of step (iv) to two to six cycles of homogenization at 500 to 1200 bars to obtain solid lipid nanoparticles of berbamine.

In the process as described herein, the temperature of step (ii) is maintained for a desired time interval.

In a preferred embodiment of the process, the mixture of the hot lipid phase and the aqueous phase of step (iv) is homogenized at 8000-12,000 rpm for 8-25 min to obtain a primary coarse emulsion.

In one embodiment of the present invention, the concentration of the surfactant in the process for preparing solid lipid nanoparticle is in the range of 2-10% w/w.

In one embodiment of the present invention, the glyceride is selected from the group consisting of mono-glycerides, di-glycerides, tri-glycerides or mixtures thereof.

In one embodiment, the glyceride is selected from the group consisting of glyceryl behenate, tricaprin, trilaurin, trimyristin, tripalmitin, tristearin, precirol, 1,2-dioctanoyl-sn-glycerol, 1,2-didecanoyl-sn-glycerol, 1,2-dilauroyl-sn-glycerol, 1,2-dimyristoyl-sn-glycerol, 1,2-dipalmitoyl-sn-glycerol, 1-palmitoyl-2-oleoyl-sn-glycerol, 1-stearoyl-2-linoleoyl-sn-glycerol, 1-stearoyl-2-arachidonoyl-sn-glycerol, 1-stearoyl-2-docosahexaenoyl-sn-glycerol, 1-oleoyl-2-acetyl-snglycerol, 1,2-di-O-phytanyl-sn-glycerol, 1,2-dipalmitoyl ethylene glycol, 1-2-dioleoyl ethylene glycol, glyceryl monostearate, behenoyl polyoxyl-8 glycerides, glyceryl palmitostearate, 1-O-hexadecyl-sn-glycerol, 1-O-hexadecyl-2-acetyl-sn-glycerol, 1-O-hexadecyl-2-O-methyl-sn-glycerol, 1,2-diacyl-3-O-(a-Dglucopyranosyl)-sn-glycerol, stearoyl macrogol-32 glycerides, stearoyl polyoxyl-32 glycerides, lauroyl macrogol-32 glycerides, lauroyl polyoxyl-32 glycerides, lauroyl macrogol-6 glycerides, lauroyl polyoxyl-6 glycerides, oleoyl macrogol-6 glycerides, oleoyl polyoxyl-6 glycerides, linoleoyl macrogol-6 glycerides, polyglyceryl-3 dioleate, glycerol monolinoleate, glyceryl monolinoleate, glycerol monooleates, diethylene glycol monoethyl ether, glyceryl dibehenate, glycerol distearate, glyceryl distearate, glyceryl dipalmitostearate, linoleoyl polyoxyl-6 glyceride, behenyl alcohol, cetyl alcohol, and potassium cetyl alcohol. In a preferred embodiment, the glyceride is glyceryl behenate or compritol.

In one embodiment of the present invention, the fatty acid is selected from the group consisting of saturated C4-C28 fatty acids and unsaturated C4-C28 fatty acids. In one of the preferred features of the present invention the fatty acid is stearic acid, lauric acid, palmitic acid, myristic acid, capric acid.

In a preferred embodiment of the present invention, the surfactant is Polysorbate 80 or Tween 80.

In one embodiment of the present invention, the co-surfactant is selected from the group consisting of soy lecithin, egg lecithin, phosphatidylcholine, cholate, glycocholate, taurocholate, taurodeoxycholate, or mixtures thereof.

In a preferred embodiment of the present invention, the co-surfactant is phospholipon 90G.

In one embodiment of the present invention, the surfactant is selected from the group consisting of ethylene oxide copolymers, propylene oxide copolymers, poloxamers, sorbitan ethylene oxide/propylene oxide copolymers, polysorbate 20, polysorbate 60, polysorbate 80, sorbitan esters, span 20, span 40, span 60, span 80, alkyllaryl polyether, alcohol polymers, tyloxapol, bile salts, cholate, glycocholate, taurocholate, taurodeoxycholate, gemini surfactants, alcohols, diethylene glycol monoethyl ether, propanediol, capryl glucoside, decyl glucoside, kolliwax or mixtures thereof.

In a preferred embodiment, the process further comprises dissolving berbamine in an emulsifier. In one of the features of the present invention the emulsifier is selected from polyethylene glycol (PEG), polyvinylpyrrolidone (PVP), polyvinyl alcohol (PVA), glycerol, transcutol, labrafac, gelucire, hydrogenated vegetable glycerides, glyceryl citrate/10 lactate/lincolate/oleate, polyglyceryl-4-cocoate, polyglyceryl-3-caprate and caprylate and their derivatives, polypropylene glycol, and propylene glycol.

In another embodiment, Polyethylene glycol (PEG 400) is used as an emulsifier for active substances and excipients. Coating with PEG, a polymer of hydrophilic nature showed better results as PEG has high hydrophilicity, chain flexibility, electrical neutrality and lack of functional groups, preventing it from interacting unnecessarily with the biological components which is very important for a suitable dosage formulation.

In an embodiment, the SLNs provide enhanced bioavailability of berbamine with high drug loading and encapsulation.

In another embodiment, the SLNs provide protection to berbamine against hydrolytic and photodegradation thereby ensuring its stability.

The particle size of berbamine loaded SLNs is in the range of 50-500 nm, with uniform particle size distribution (Polydispersity index≤0.4) and a capacity for solubilisation, high permeation across biological membranes, photoprotection, thereby, enhancing its therapeutic efficacy.

The process as defined in the present invention results in the berbamine loaded SLNs with high berbamine loading (12-50% w/w with respect to the lipid phase/matrix; 0.5-10% w/w berbamine in the aqueous SLN dispersion), significant entrapment >90%), and small size (50-500 nm).

The present invention also relates to solid lipid nanoparticles of berbamine prepared by the process defined herein.

The solid lipid nanoparticles of berbamine comprise a. lipid phase comprising mixture of lipid selected from group consisting of glycerides and fatty acids;
b. an aqueous phase comprising water, surfactant and co surfactant, wherein berbamine is entrapped in lipid phase and is present in a solubilised form in the aqueous phase and the two are in equilibrium.

The SLNs for berbamine have been prepared using low concentration of surfactant with high drug loading and encapsulation efficiency with scalable and industrially viable techniques. The method does not involve usage of organic solvents. The formulation is an aqueous dispersion and is water soluble and water washable.

In another embodiment, all ingredients used in preparing berbamine loaded SLNs were of GRAS status in order to provide safe SLNs.

The solid lipid nanoparticles of berbamine have a particle size in the range of 50-500 nm. The solid lipid nanoparticles of berbamine prepared by the process of the present invention have a uniform particle size distribution.

The solid lipid nanoparticles of berbamine as prepared by the process of the present invention have a spherical shape.

The SLNs of berbamine, prepared by the process of present invention can be in the form of dispersion, gel, hydrogel, organogel, syrup, paste, cream, liquid wash, facewash, mouthwash, oral rinse, ointment, liquid ampoule, nasal drops/spray, ear drops, aerosol spray, powder, orthotic aid, liquid oral, facemask, film, implant, tablet, lozenges, capsules, suppositories, pessaries, patch and gummies.

The SLNs of berbamine are in the form of a dispersion for oral, parenteral, ocular, intranasal, dental, buccal, vaginal, rectal, otic, transdermal and topical delivery.

The solid lipid nanoparticles of berbamine show burst release of berbamine for initial 2 h and controlled release up to 48 hours.

The present process achieved high loading of berbamine (25% with respect to the lipid phase; high concentration 1% w/v of berbamine in the aqueous SLN dispersion) significant entrapment efficiency (96%±0.56%), and small size (average particle size 206.1 nm; PDI—0.381). The resulting formulation was nanosized (100-300 nm), with uniform particle size distribution (Polydispersity index<0.4) and a capacity for solubilisation, high permeation across biological membranes, photoprotection and protection against degradation at alkaline and physiological pH, of berbamine, thereby increasing its bioavailability.

The lipid core provides protection to berbamine against oxidation, and hydrolytic and photo degradation in addition to providing berbamine in a bioavailable and controlled manner. Biocompatible, cheap, FDA approved easily available components including a lipid, non-ionic surfactants and surfactant supporting agents/co-solvents have been used. The efficient entrapment of berbamine within the core of these nanoparticles in a solubilised form increases its efficacy.

The SLNs enhance the stability and efficacy of berbamine, reduce the dose and may show greater promise not only as potential antiviral-cum-antibacterial agent but also in a clinically presentable and useful dosage form.

In yet another aspect, the formulation is used for treating diabetes and more specifically for treating diabetes associated complications such as one or more of cardiovascular complications, diabetic retinopathy, diabetic nephropathy, diabetic polyneuropathies, thyroid disorders, skin conditions, hearing impairment, foot complications such as leg ulcers and diabetic foot, diabetic wounds, liver diseases and reduced immunity.

In yet another embodiment, the diabetic wound is an acute or chronic wound.

In yet another aspect, the formulation can be used as a wound healer, as an antimicrobial, as an anti-inflammatory agent and for the treatment of microbial infections especially resistant to *Acinetobacter* infections.

Further, SLNs exhibit any therapeutic property identical to free berbamine.

The advantages of the present invention include:

1. Method of preparation ensures that berbamine is stabilised.
2. High entrapment efficiency>90%.
3. Water soluble and washable system.
4. High drug loading (25%).
5. Method is easy, scalable, and commercially viable and uses equipment such as homogenizer which are normally present in any pharmaceutical industry.
6. All the employed components are GRAS.
7. The SLNs of berbamine are in the form of a dispersion for oral, parenteral, ocular, dental, buccal, intranasal, vaginal, rectal, otic, transdermal and topical delivery.

EXAMPLES

The present disclosure with reference to the accompanying examples describes the present invention. However, those of skill in the art should, in light of the present disclosure, appreciate that many changes can be made in the specific embodiments which are disclosed and still obtain a like or similar result without departing from the spirit and scope of the invention. It is understood that the examples are provided for the purpose of illustrating the invention only, and are not intended to limit the scope of the invention in any way.

The berbamine used in the present invention can be procured from different commercial sources as well as it can also be isolated from different species of *Berberis, Mahonia, Cyclea, Thalictrum* and in *Pycnarrhena novoguineensis, Stephania cepharantha, Atherosperma moshatum*. The bis-benzylisoquinoline alkaloids-enriched fraction from plant extract can also be used as it contains berbamine and related alkaloids.

Example 1

TABLE 1

| Vesicular systems | | | | | |
|---|---|---|---|---|---|
| Lipophilic phase | | | | Hydrophilic phase | |
| Ethanol (mL) | Span 40 (mg) | Span 60 (mg) | Span 80 (mg) | PEG 400 (g) | Water (mL) |
| 10 | 78 | — | — | 3.2 | 8.8 |
| 10 | 80 | — | — | 5 | 5 |
| 9 | — | 40 | 40 | 2 | 9 |
| 10 | — | 40 | 40 | 2 | 8 |
| 10 | — | 40 | 40 | 0.5 | 9.5 |

Example 2

Preparation of Berbamine Loaded Solid Lipid Nanoparticles (SLNs) by High Pressure Homogenization Method:

The formulation of nanoparticles was prepared by using hot homogenization technique. Phospholipon 90G (0.4 g), tween 80 (8 g) and water (72.6 mL) were taken together in a beaker and heated to the lipid melting temperature. The lipid, Compritol® 888 ATO (6 g) was melted separately at 82° C. Berbamine (3 g) was dissolved in PEG 400 (10 g). This dissolved berbamine was then added to the lipid phase and the pH of this composition was 6.5. The hot lipid phase was dropped at once into the aqueous phase under high-speed homogenization at 18000 rpm for 10 minutes. The hot emulsion thus formed was passed through homogenizer at 1200 bars pressure and three cycles were run. The formulation so formed was cooled to room temperature, for an hour, to allow lipidic particles to solidify after which it was refrigerated.

The blank SLNs were prepared following the same method without addition of berbamine.

Incorporation of SLNs into Gel System

Carbopol 2 g was dispersed in 10 mL of water and kept overnight for swelling. Two to three drops of triethanolamine were added to this mixture with continuous stirring, to affect the gelling of carbopol. Stirring was continued until a translucent gel was formed. Then 88 mL of berbamine loaded SLNs dispersion was added separately to the prepared gel and mixed slowly to obtain a homogeneous mixture containing carbopol. Blank SLNs gel was prepared by incorporation of berbamine free SLNs dispersed in 88 mL of double distilled water instead of berbamine loaded SLNs dispersion in similar way.

Example 3

Preparation of Berbamine Loaded Solid Lipid Nanoparticles (SLNs) by High Pressure Homogenization Method:

The formulation of nanoparticles was prepared by using hot homogenization technique. Phospholipon 90G (0.4 g), tween 80 (10 g) and water (81.6 mL) were taken together in a beaker and heated to the lipid melting temperature. The lipid, Compritol® 888 ATO (6 g) was melted separately at 82° C. Berbamine (2 g) was then added to the lipid phase and the pH of this composition was 6.3. The hot lipid phase was dropped at once into the aqueous phase under high speed homogenization at 10000 rpm for 15 minutes. The hot emulsion thus formed was passed through homogenizer at 1000 bars pressure and three cycles were run. The formulation so formed was cooled to room temperature, for an hour, to allow lipidic particles to solidify after which it was refrigerated.

The blank SLNs were prepared following the same method without addition of berbamine.

Incorporation of SLNs into Gel System

Carbopol 1.5 g was dispersed in 10 mL of water and kept overnight for swelling. Two to three drops of triethanolamine were added to this mixture with continuous stirring, to affect the gelling of carbopol. Stirring was continued until a translucent gel was formed. Then 88.5 mL of berbamine loaded SLNs dispersion was added separately to the prepared gel and mixed slowly to obtain a homogeneous mixture containing carbopol. Blank SLNs gel was prepared by incorporation of berbamine free SLNs dispersed in 88.5 mL of double distilled water instead of berbamine loaded SLNs dispersion in similar way.

Example 4

Preparation of Berbamine Loaded Solid Lipid Nanoparticles (SLNs) by High Pressure Homogenization Method:

The formulation of nanoparticles was prepared by using hot homogenization technique. Phospholipon 90G (0.4 g), tween 80 (8 g) and water (78.1 mL) were taken together in a beaker and heated to the lipid melting temperature. The lipid, Stearic acid (4.5 g) was melted separately at 70° C. Berbamine (1 g) was dissolved in PEG 400 (8 g). This dissolved berbamine was then added to the lipid phase and pH of this composition was 6. The hot lipid phase was dropped at once into the aqueous phase under high-speed homogenization at 8000 rpm for 20 minutes. The hot emulsion thus formed was passed through homogenizer at 800 bars pressure and three cycles were run. The formulation so formed was cooled to room temperature, for an hour, to allow lipidic particles to solidify after which it was refrigerated.

The blank SLNs were prepared following the same method without addition of berbamine. Incorporation of SLNs into gel system Carbopol 1 g was dispersed in 10 mL of water and kept overnight for swelling. Two to three drops of triethanolamine were added to this mixture with continuous stirring, to affect the gelling of carbopol. Stirring was continued until a translucent gel was formed. Then 89 mL of berbamine loaded SLNs dispersion was added separately to the prepared gel and mixed slowly to obtain a homogeneous mixture containing carbopol. Blank SLNs gel was prepared by incorporation of berbamine free SLNs dispersed in 89 mL of double distilled water instead of berbamine loaded SLNs dispersion in similar way.

Example 5

Preparation of Berbamine Loaded Solid Lipid Nanoparticles (SLNs) by High Pressure Homogenization Method:

The formulation of nanoparticles was prepared by using hot homogenization technique. Phospholipon 90G (0.4 g), tween 80 (9 g) and water (78.1 mL) were taken together in a beaker and heated to the lipid melting temperature. The lipid, Precirol (3 g) was melted separately. Berbamine (1.5 g) was dissolved in PEG 400 (8 g). This dissolved berbamine was then added to the lipid phase and the pH of this composition was 6.5. The hot lipid phase was dropped at once into the aqueous phase under high-speed homogenization at 12000 rpm for 25 minutes. The hot emulsion thus formed was passed through homogenizer at 500 bars pressure and two cycles were run. The formulation so formed was cooled to room temperature, for an hour, to allow lipidic particles to solidify after which it was refrigerated.

The blank SLNs were prepared following the same method without addition of berbamine.

Incorporation of SLNs into Gel System

Carbopol 0.5 g was dispersed in 10 mL of water and kept overnight for swelling. Two to three drops of triethanolamine were added to this mixture with continuous stirring, to affect the gelling of carbopol. Stirring was continued until a translucent gel was formed. Then 89.5 mL of berbamine loaded SLNs dispersion was added separately to the prepared gel and mixed slowly to obtain a homogeneous mixture containing carbopol. Blank SLNs gel was prepared by incorporation of berbamine free SLNs dispersed in 89.5 mL of double distilled water instead of berbamine loaded SLNs dispersion in similar way.

Example 6

Preparation of Berbamine Loaded Solid Lipid Nanoparticles (SLNs) by High Pressure Homogenization Method:

The formulation of nanoparticles was prepared by using hot homogenization technique. Phospholipon 90G (0.4 g), tween 80 (8 g) and water (78.6 mL) were taken together in a beaker and heated to the lipid melting temperature. The lipid, Glycerol monostearate (4 g) was melted separately. Berbamine (1 g) was dissolved in PEG 400 (8 g). This dissolved berbamine was then added to the lipid phase and the pH of this composition was 6.3. The hot lipid phase was dropped at once into the aqueous phase under high-speed homogenization at 8000 rpm for 10 minutes. The hot emulsion thus formed was passed through homogenizer at 1000 bars pressure and three cycles were run. The formulation so formed was cooled to room temperature, for an hour, to allow lipidic particles to solidify after which it was refrigerated.

The blank SLNs were prepared following the same method without addition of berbamine.

Incorporation of SLNs into Gel System

Carbopol 1.5 g was dispersed in 10 mL of water and kept overnight for swelling. Two to three drops of triethanolamine were added to this mixture with continuous stirring, to affect the gelling of carbopol. Stirring was continued until a translucent gel was formed. Then 88.5 mL of berbamine loaded SLNs dispersion was added separately to the prepared gel and mixed slowly to obtain a homogeneous mixture containing carbopol. Blank SLNs gel was prepared by incorporation of berbamine free SLNs dispersed in 88.5 mL of double distilled water instead of berbamine loaded SLNs dispersion in similar way.

Example 7

Preparation of Berbamine Loaded Solid Lipid Nanoparticles (SLNs) by High Pressure Homogenization Method:

The formulation of nanoparticles was prepared by using hot homogenization technique. Berbamine (0.5 g) was dissolved in water (78 mL) and pH was maintained at 7.8. Phospholipon 90G (0.5 g), tween 80 (10 g) and PEG 400 (9 g) were taken together with water and heated to the lipid melting temperature. The lipid, Compritol® 888 ATO (2 g)

was melted separately at 82° C. The hot lipid phase was dropped at once into the aqueous phase under high-speed homogenization at 8000 rpm for 15 minutes. The hot emulsion thus formed was passed through homogenizer at 1000 bars pressure and three cycles were run. The formulation so formed was cooled to room temperature, for an hour, to allow lipidic particles to solidify after which it was refrigerated.

The blank SLNs were prepared following the same method without addition of berbamine.

Incorporation of SLNs into Gel System

Carbopol 1 g was dispersed in 10 mL of water and kept overnight for swelling. Two to three drops of triethanolamine were added to this mixture with continuous stirring, to affect the gelling of carbopol. Stirring was continued until a translucent gel was formed. Then 89 mL of Berbamine loaded SLNs dispersion was added separately to the prepared gel and mixed slowly to obtain a homogeneous mixture containing carbopol. Blank SLNs gel was prepared by incorporation of berbamine free SLNs dispersed in 89 mL of double distilled water instead of berbamine loaded SLNs dispersion in similar way.

Example 8

Preparation of Berbamine Loaded Solid Lipid Nanoparticles (SLNs) by High Pressure Homogenization Method:

The formulation of nanoparticles was prepared by using hot homogenization technique. Phospholipon 90G (0.8 g), tween 80 (12 g) and water (77.2 mL) were taken together in a beaker and heated to the lipid melting temperature. The lipid, Compritol® 888 ATO (4 g) was melted separately at 82° C. Berbamine (1 g) was dissolved in PEG 400 (5 g). This dissolved berbamine was then added to the lipid phase. The hot lipid phase was dropped at once into the aqueous phase under high-speed homogenization at 8000 rpm for 25 minutes. The hot emulsion thus formed was passed through homogenizer at 1000 bars pressure and three cycles were run. The formulation so formed was cooled to room temperature, for an hour, to allow lipidic particles to solidify after which it was refrigerated.

The blank SLNs were prepared following the same method without addition of berbamine.

Incorporation of SLNs into Gel System

Carbopol 2 g was dispersed in 10 mL of water and kept overnight for swelling. Two to three drops of triethanolamine were added to this mixture with continuous stirring, to affect the gelling of carbopol. Stirring was continued until a translucent gel was formed. Then 88 mL of Berbamine loaded SLNs dispersion was added separately to the prepared gel and mixed slowly to obtain a homogeneous mixture containing carbopol. Blank SLNs gel was prepared by incorporation of berbamine free SLNs dispersed in 88 mL of double distilled water instead of berbamine loaded SLNs dispersion in similar way.

Example 9

Preparation of Berbamine Loaded Solid Lipid Nanoparticles (SLNs) by High Pressure Homogenization Method:

The formulation of nanoparticles was prepared by using hot homogenization technique. Phospholipon 90G (0.2 g), tween 80 (5 g) and water (76.3 mL) were taken together in a beaker and heated to the lipid melting temperature. The lipid, Compritol® 888 ATO (4 g) was melted separately at 82° C. Berbamine (2.5 g) was dissolved in PEG 400 (12 g). This dissolved berbamine was then added to the lipid phase such that the pH of the composition was 6.3. The hot lipid phase was dropped at once into the aqueous phase under high-speed homogenization at 8000 rpm for 15 minutes. The hot emulsion thus formed was passed through homogenizer at 1000 bars pressure and three cycles were run. The formulation so formed was cooled to room temperature, for an hour, to allow lipidic particles to solidify after which it was refrigerated.

The blank SLNs were prepared following the same method without addition of berbamine.

Incorporation of SLNs into Gel System

Carbopol 1 g was dispersed in 10 mL of water and kept overnight for swelling. Two to three drops of triethanolamine were added to this mixture with continuous stirring, to affect the gelling of carbopol. Stirring was continued until a translucent gel was formed. Then 89 mL of Berbamine loaded SLNs dispersion was added separately to the prepared gel and mixed slowly to obtain a homogeneous mixture containing carbopol. Blank SLNs gel was prepared by incorporation of berbamine free SLNs dispersed in 89 mL of double distilled water instead of berbamine loaded SLNs dispersion in similar way.

Example 10

Preparation of Berbamine Loaded Solid Lipid Nanoparticles (SLNs) by High Pressure Homogenization Method:

The formulation of nanoparticles was prepared by using hot homogenization technique. Phospholipon 90G (1 g), tween 80 (10 g), PEG 400 (8 g) and water (76.5 mL) were taken together in a beaker and heated to the lipid melting temperature. Berbamine (1.5 g) was added to this aqueous phase with pH of 8.3. The lipid, Compritol® 888 ATO (3 g) was melted separately at 82° C. The hot lipid phase was dropped at once into the aqueous phase under high-speed homogenization at 8000 rpm for 10 minutes. The hot emulsion thus formed was passed through homogenizer at 1000 bars pressure and three cycles were run. The formulation so formed was cooled to room temperature, for an hour, to allow lipidic particles to solidify after which it was refrigerated.

The blank SLNs were prepared following the same method without addition of berbamine.

Incorporation of SLNs into Gel System

Carbopol 0.5 g was dispersed in 10 mL of water and kept overnight for swelling. Two to three drops of triethanolamine were added to this mixture with continuous stirring, to affect the gelling of carbopol. Stirring was continued until a translucent gel was formed. Then 89.5 mL of Berbamine loaded SLNs dispersion was added separately to the prepared gel and mixed slowly to obtain a homogeneous mixture containing carbopol. Blank SLNs gel was prepared by incorporation of berbamine free SLNs dispersed in 89.5 mL of double distilled water instead of berbamine loaded SLNs dispersion in similar way.

Example 11

Preparation of Berbamine Loaded Solid Lipid Nanoparticles (SLNs) by High Pressure Homogenization The formulation of nanoparticles was prepared using hot homogenization technique. Phospholipon 90G, tween 80, and water were taken together in a beaker and heated to the lipid melting temperature. The lipid, Compritol® 888 ATO was melted separately at 82° C. The hot lipid phase was dropped all at once into the aqueous phase under speed homogenization at 8000 rpm for 15 minutes. Berbamine solution was added to this hot emulsion under speed homogenization at 15000 rpm for 5 min thereafter emulsion was passed through homogenizer at 1000 bars pressure and three cycles were run. The formulation so formed was cooled to room temperature, for an hour, to allow lipidic particles to solidify after which it was refrigerated. The pH of the final formulation was 5.8.

Incorporation of SLNs into Gel System

Carbopol 1.5 g was dispersed in 10 mL of water and kept overnight for swelling. Two to three drops of triethanolamine were added to this mixture with continuous stirring, to affect the gelling of carbopol. Stirring was continued until a translucent gel was formed. Then 88.5 mL of berbamine loaded SLNs dispersion was added separately to the prepared gel and mixed slowly to obtain a homogeneous mixture containing carbopol. Blank SLNs gel was prepared by incorporation of berbamine free SLNs dispersed in 88.5 mL of double distilled water instead of berbamine loaded SLNs dispersion in similar way.

Example 12

Preparation of Berbamine Loaded Solid Lipid Nanoparticles (SLNs) by High Pressure Homogenization The formulation of nanoparticles prepared using hot homogenization technique. Phospholipon 90G, tween 80, PEG 400 and water were taken together in a beaker and berbamine was dissolved in this aqueous phase at pH 8.1 and heated to the lipid melting temperature. The lipid, Compritol® 888 ATO was melted separately at 82° C. The hot lipid phase was once dropped into the aqueous phase under speed homogenization at 8000 rpm for 15 minutes and this hot emulsion was passed through homogenizer at 1000 bars pressure and three cycles were run. The formulation so formed was cooled to room temperature, for an hour, to allow lipidic particles to solidify after which it was refrigerated.

Incorporation of SLNs into Gel System

Carbopol 1.5 g was dispersed in 10 mL of water and kept overnight for swelling. Two to three drops of triethanolamine were added to this mixture with continuous stirring, to affect the gelling of carbopol. Stirring was continued until a translucent gel was formed. Then 88.5 mL of berbamine loaded SLNs dispersion was added separately to the prepared gel and mixed slowly to obtain a homogeneous mixture containing carbopol. Blank SLNs gel was prepared by incorporation of berbamine free SLNs dispersed in 88.5 mL of double distilled water instead of berbamine loaded SLNs dispersion in similar way.

Example 13

Preparation of Berbamine Loaded Solid Lipid Nanoparticles (SLNs) by High Pressure Homogenization The formulation of nanoparticles was done using hot homogenization technique. Phospholipon 90 G, tween 80 and water were taken together in a beaker and heated to the lipid melting temperature to obtain an aqueous phase. The lipid, Compritol® 888 ATO was melted separately at 82° C. to obtain a lipid phase. Berbamine was added to the lipid phase by continuous stirring and the pH of the composition was adjusted to maintain the pH at 6.2. The hot lipid phase was once dropped into the aqueous phase under speed homogenization at 8000 rpm for 20 minutes to obtain a hot emulsion. The hot emulsion thus formed was passed through homogenizer at 1000 bars pressure and three cycles were run. The formulation so formed was cooled to room temperature, for an hour, to allow lipidic particles to solidify after which it was refrigerated.

Incorporation of SLNs into Gel System

Carbopol 1.5 g was dispersed in 10 mL of water and kept overnight for swelling. Two to three drops of triethanolamine were added to this mixture with continuous stirring, to affect the gelling of carbopol. Stirring was continued until a translucent gel was formed. Then 88.5 mL of berbamine loaded SLNs dispersion was added separately to the prepared gel and mixed slowly to obtain a homogeneous mixture containing carbopol. Blank SLNs gel was prepared by incorporation of berbamine free SLNs dispersed in 88.5 mL of double distilled water instead of berbamine loaded SLNs dispersion in similar way.

Example 14

Characterization of SLNs

Optical Microscopy

SLNs were characterized preliminarily using optical microscope after suitable dilution with distilled water. The optical inspection of berbamine loaded SLNs indicated these to be small and round in shape, with no aggregation/irregularities in general as shown in FIG. 1.

Field Emission Scanning Electron Microscopy (FESEM)

SLNs of berbamine were observed microscopically using FESEM for uniformity of size, shape and physical stability characteristic i.e. aggregation or irregularity. SLNs dispersions of berbamine was placed on Nucleopore Track-Etch membrane and kept for drying at room temperature. Further, silicon wafer was attached to the dried membrane followed by sputter coating with platinum. Images were taken at the −140° C. and a voltage of 15 kV using field emission scanning electron microscope (FESEM).

Figure 2:
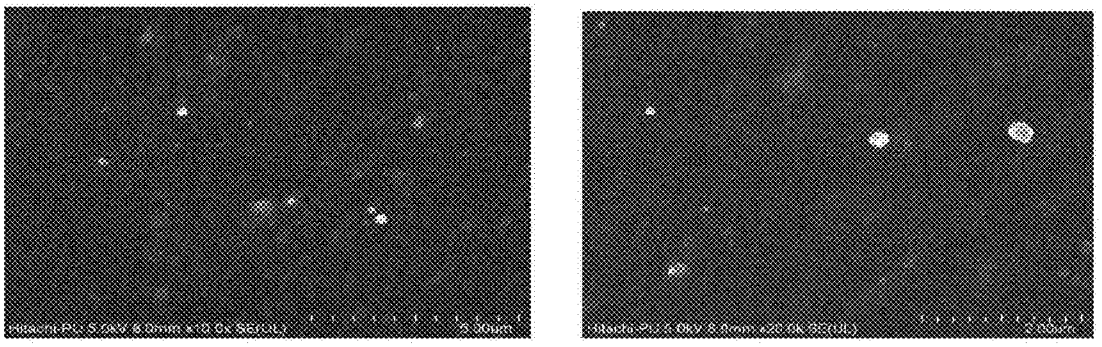
FIG. 2: illustrates FESEM of berbamine SLNs.

FESEM of berbamine loaded SLNs depicted that particles were spherical in shape and are under nanoscale range as shown in FIG. 2. The particles were present as an individual entity rather than aggregates confirming their stability.

Figure 3:
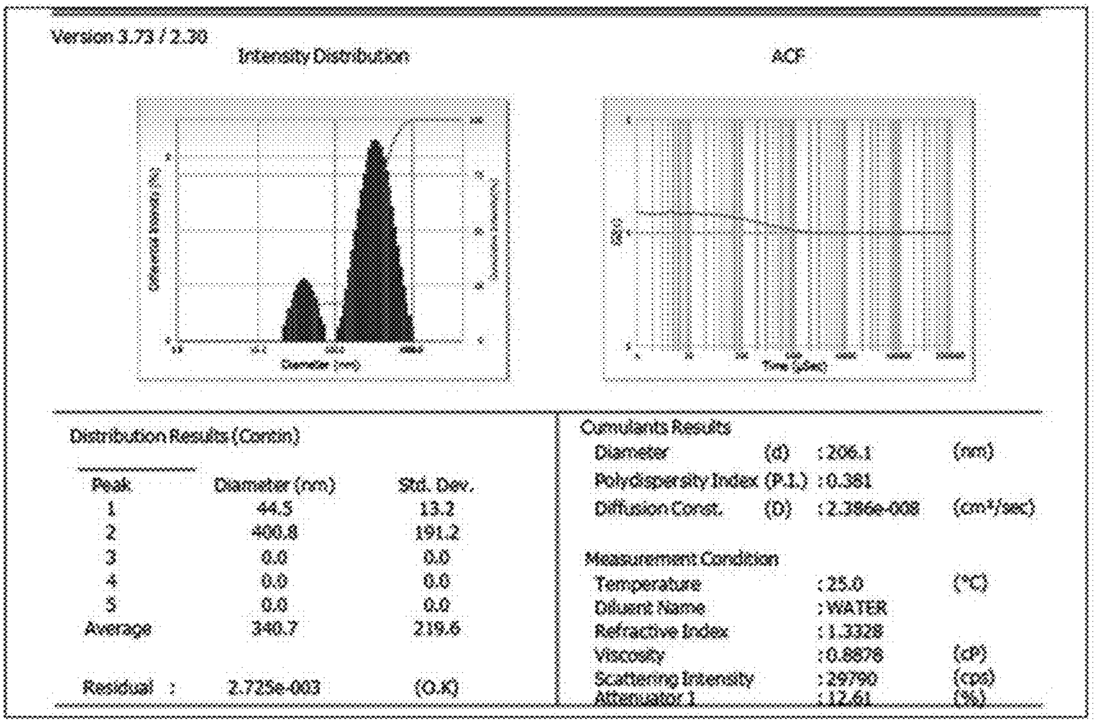
FIG. 3: illustrates A. Particle size of berbamine SLNs; B. Particle size of berbamine loaded SLNs (After 8 months)
Figure 3:
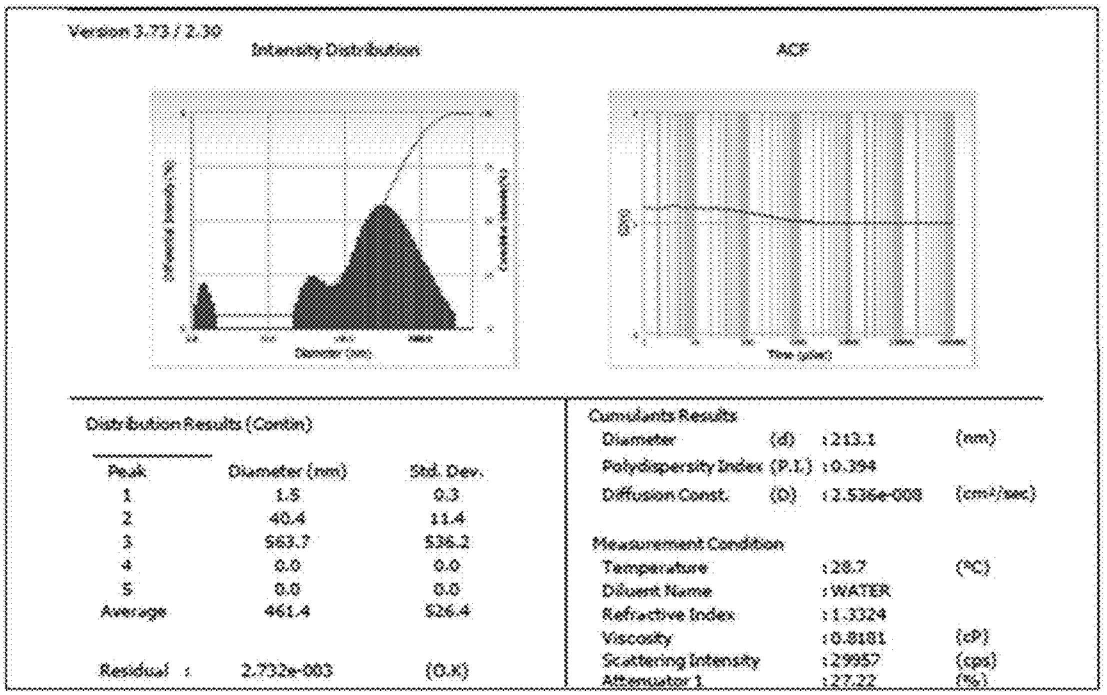

The developed berbamine loaded SLNs showed an average particle size of 206 nm and PDI of 0.381 (FIG. 3 A). After 8 months, berbamine loaded SLNs showed particle size of 213 nm with PDI of 0.394 (FIG. 3 B) which showed the stability of the developed SLNs system.

Assay/total Drug Content (TDC)

The TDC of SLNs was determined by disrupting 1 mL of the dispersion using mixture of chloroform-methanol (1:1) using vortex and the solution thus obtained was filtered through Whatman filter paper to obtain a clear solution. The obtained solutions were analysed spectrophotometrically at $\lambda_{max}$ 284 nm for berbamine SLNs formulation using chloroform-methanol (1:1) as blank. TDC was calculated by using the following equation:

$$\text{Total drug content(mg)} = \frac{\text{Absorbance} * 10 * \text{Dilution factor}}{E^{1\%}_{1\ cm}}$$

$$\text{Total drug content(\%)} = \frac{\text{Actual drug content(mg)}}{\text{Theortical drug content(mg)}} \times 100$$

Assay/total drug content of berbamine in berbamine SLNs was 94±0.38%. High values (approaching 100%) of TDC are indicative of the insignificant loss incurred during the process of preparation of SLNs.

Determination of Entrapment Efficiency (EE)

The EE of the prepared SLNs of both samples was determined by using dialysis membrane having pore size 2.4 nm, molecular weight cut off 12-14 KD. Membrane was soaked in double distilled water for 12 h prior to use.

For berbamine loaded SLNs dispersion, 0.5 mL was placed in this pre-soaked dialysis tubing, which was hermetically sealed, and dialyzed against 100 mL methanol at room temperature for 2 h.

Berbamine SLNs prepared at different pHs are evaluated for entrapment efficiency.

TABLE 2

Effect of pH on Entrapment Efficiency

| Formulation | Berbamine loading | pH | Diameter (nm) | Entrapment Efficiency |
|---|---|---|---|---|
| BBM1 | 1% in aqueous phase | 7.5 | 188 | 95% |
| BBM2 | 1% in aqueous phase | 6.5 | 195 | 88% |
| BBM3 | 1% in aqueous phase | 5.5 | 214 | 78% |
| BBM4 | 1% in lipid phase | 5.5 | 199 | 76% |
| BBM5 | 1% in lipid phase | 6.5 | 204 | 96% |
| BBM6 | 1% in lipid phase | 7.5 | 185 | 85% |

It has been observed that the entrapment efficacy of berbamine loaded SLNs is maximum, when the pH was kept around 7.5 to 8.5 when berbamine is dissolved in water phase and pH was kept around 6.0 to 7.0, when berbamine is dissolved in lipid phase as given in Table 2. Entrapment efficiency (EE) of berbamine loaded SLNs was 96±1%. Higher EE indicates the suitability of the method used for the preparation of SLNs.

Zeta Potential

Zeta potential of SLNs dispersions (10×) dilution was measured using Beckman zetasizer, at 25° C. and the electric field strength of 23.2 V/cm, using high concentration cell. The zetasizer measures the zeta potential based on the Smoluchowski equation.

Figure 4:
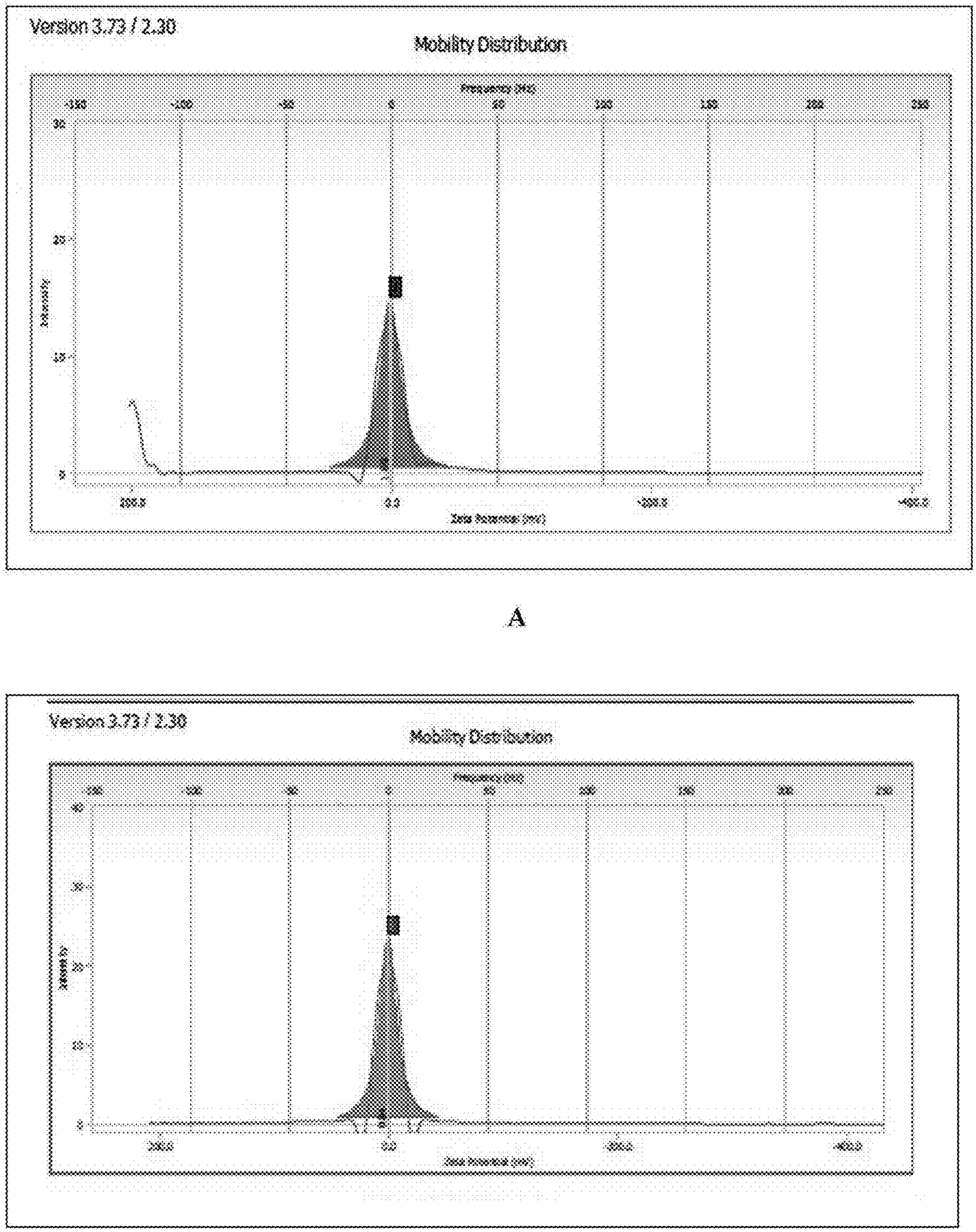
FIG. 4: illustrates A. Zeta potential of berbamine SLNs, B. Zeta potential of berbamine loaded SLNs (After 8 months)

The observed zeta potential of berbamine formulation was 1.69 mV (FIG. 4 A). After 8 months zeta potential of berbamine loaded SLNs was 0.84 mV (FIG. 4 B). The near neutral zeta potential is reported to result in stable particles.

In Vitro Release Studies

In-vitro release studies were performed using Franz diffusion assembly. Dialysis membrane with a molecular weight cut-off of 12000-14000 Da were soaked in double distilled water for 12 hours. Ethanol:phosphate buffer pH 6.8 (30:70) was taken as release medium. The release medium (30 mL) in each cell was maintained at 37° C. and stirred throughout the time of experiment. The dialysis membrane was loaded with 0.5 mL of SLNs dispersion. Aliquots of 0.5 mL were withdrawn at different time intervals for 72 h and replenished with same volume of release medium. The collected samples were suitably diluted and analysed by UV-visible spectrophotometer.

Figure 5:
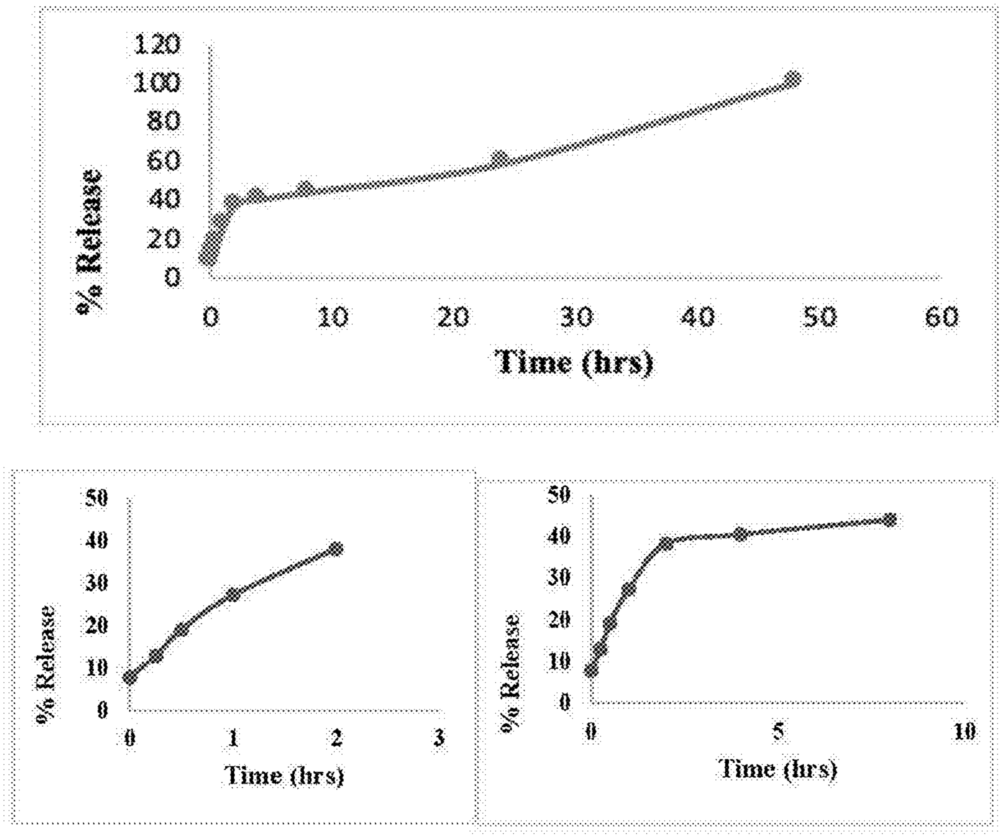
FIG. 5: illustrates in vitro release of berbamine SLNs, A. Phase I of fast drug release for initial 2 hrs, B. Phase II of controlled release of drug from 2 to 8 hrs.

In vitro release profile reveals fundamental information on the drug delivery system form and its behaviour. It also provides detail of the release mechanism and kinetics enabling a rational and scientific approach to drug product development. For berbamine loaded SLNs nearly 100% drug was released in 48 hours as depicted in FIG. 5.

FT-IR

The FT-IR spectra (Agilent Technologies 630 Cary, USA) of berbamine, berbamine loaded SLNs, Compritol® 888 ATO, phospholipon 90G and physical mixture of Compritol® 888 ATO with PEG 400 melted and solidified were obtained, using Micro Lab software. Samples were analysed over the range 400-4000 $cm^{-1}$.

Figure 6:
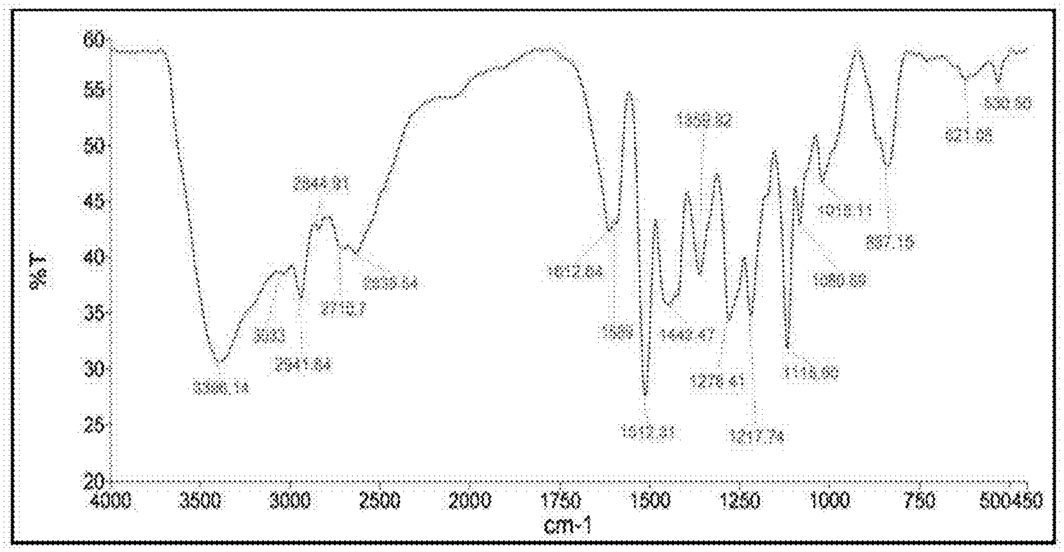
FIG. 6: illustrates FT-IR spectra of a) berbamine, b) berbamine loaded SLNs c) Compritol® 888 ATO, d) phospholipon 90 G e) physical mixture of Compritol® 888 ATO and PEG 400 (melted and solidified).
Figure 6:
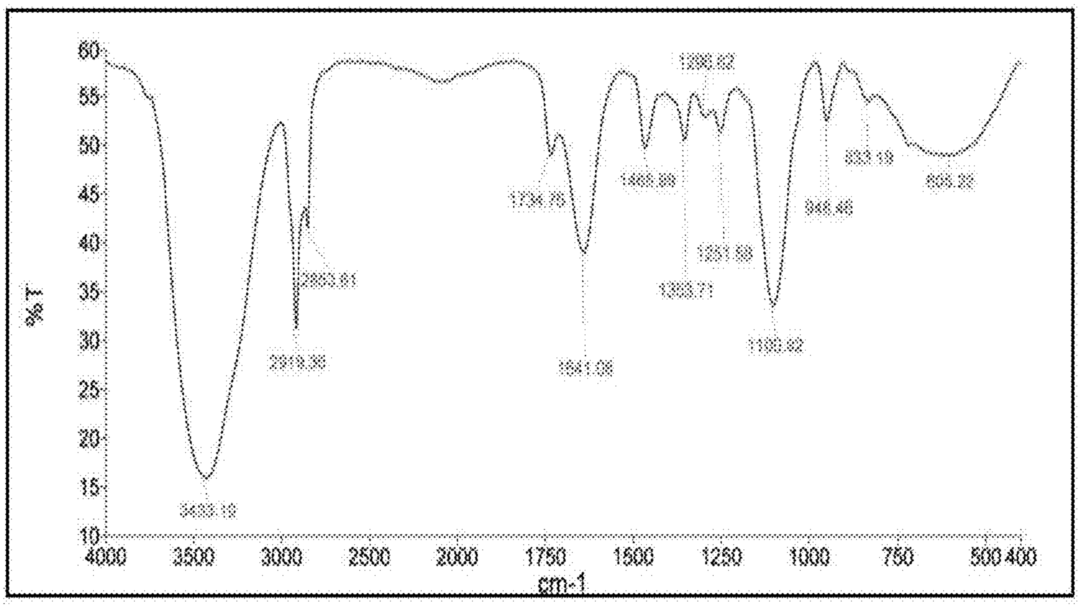
Figure 6:
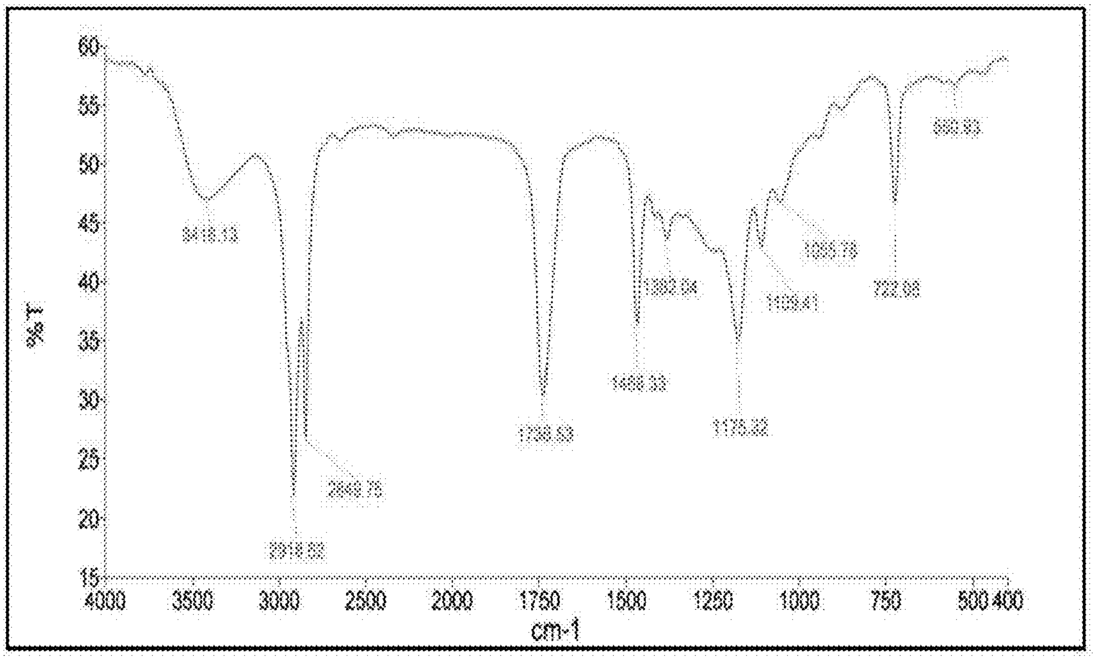
Figure 6:
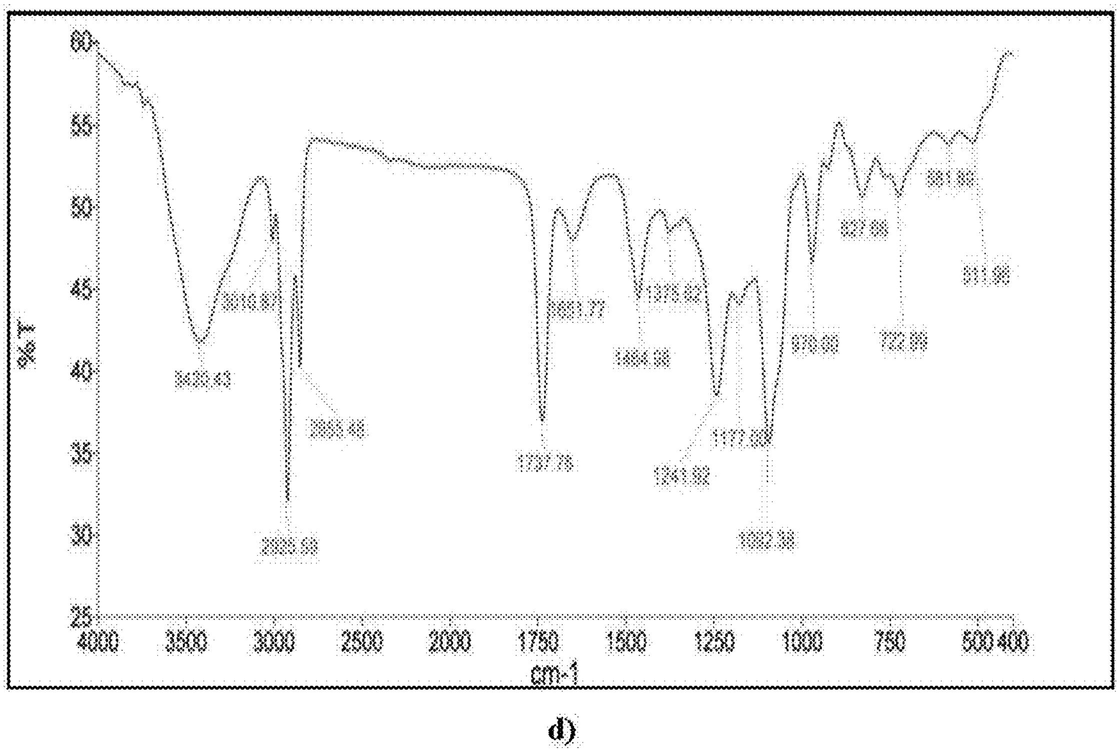
Figure 6:
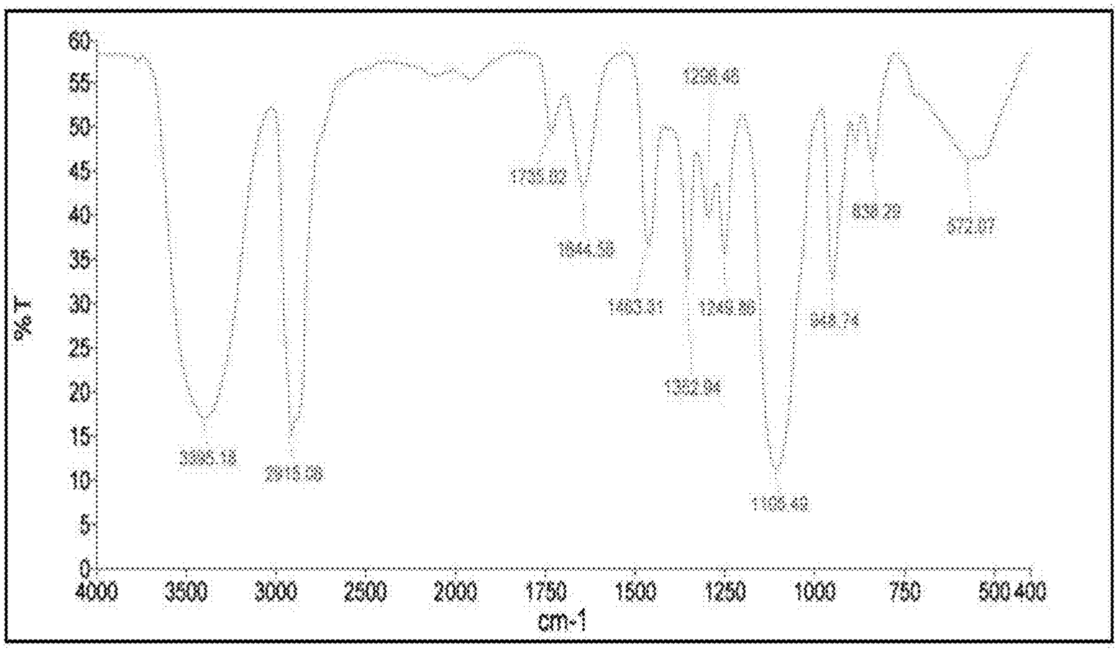

FT-IR spectra of berbamine, berbamine SLNs, Compritol® 888 ATO, Phospholipon 90 G and physical mixture of Compritol® 888 ATO and PEG 400 (melted and solidified) are shown in FIG. 6. Pure berbamine showed characteristic peaks at 1512 $cm^{-1}$ (C—N stretch), 1278 $cm^{-1}$ and 1115.60 $cm^{-1}$ due to aryl alkyl ether (C—O—C). Compritol® 888 ATO showed characteristic peaks at 2919 $cm^{-1}$ and 2850 $cm^{-1}$ (alkane stretch) and 1738 $cm^{-1}$ (ethers stretch). All characteristic absorption bands of berbamine, Compritol®888 ATO were observed in berbamine loaded SLNs and reduction in the sharpness of some peaks was observed. The spectra of Compritol® 888 ATO and PEG 400 melted and solidified showed no signifying interaction between the two even on heating. This confirmed that both these components retain their individual properties when incorporated in nanoparticles. The retention of characteristic peaks suggested absence of interaction of the components.

Differential Scanning Calorimetry (DSC)

DSC thermographs of berbamine, berbamine loaded SLNs, Compritol® 888 ATO were recorded to evaluate any significant shift or disappearance/appearance of new peaks. Different lipid modifications possess different melting points and enthalpies which provides information regarding sample structure and interactions between the components. The samples (2-5 mg) were scanned using crimped aluminium pans. The temperature range was varied from 30° C. to 350° C. at the heating rate of 10° C./min.

Figure 7:
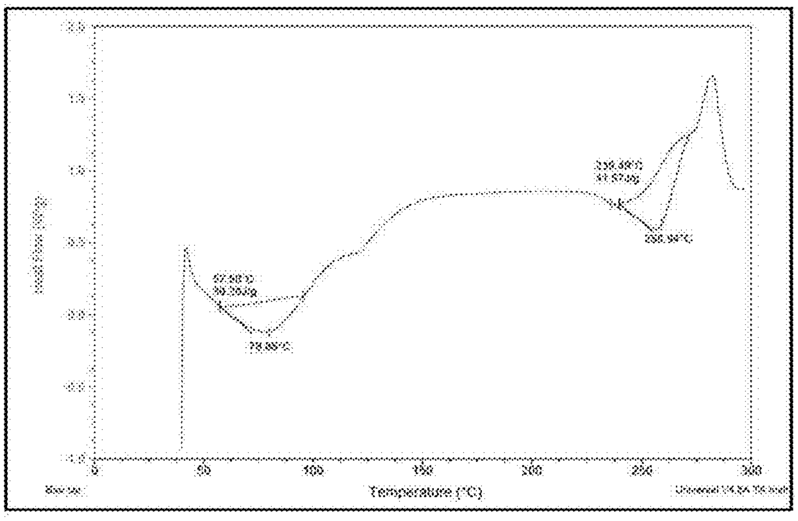
FIG. 7: illustrates DSC thermograms of a) berbamine, b) Compritol® 888 ATO and c) berbamine SLNs.
Figure 7:
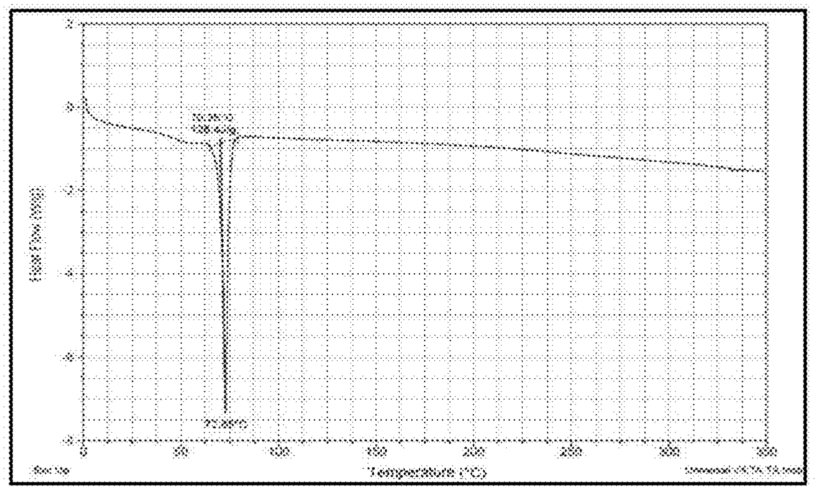
Figure 7:
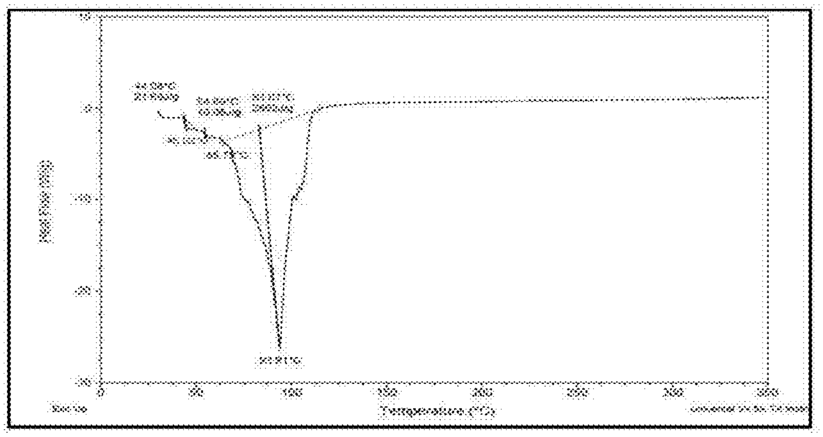

DSC thermograms of berbamine, berbamine loaded SLNs and Compritol® 888 ATO are shown in FIG. 7. DSC was performed to investigate the melting behaviour of crystalline materials. DSC thermogram of berbamine showed broad endotherm at 79.85° C. Compritol® 888 ATO showed sharp endotherm at 72.85° C. Berbamine loaded SLNs showed sharp peak at 93.91° C. along with disappearance of the peaks observed in berbamine thermogram. This suggest the molecular dispersion of berbamine into the loaded SLNs and that they exist in amorphous state. The disappearance of the peaks also indicated their efficient entrapment in the lipid matrix.

PXRD

PXRD was performed using XPERT-PRO diffractometer system (PANalytical, Netherlands) with a CuKα radiation (1.54060 Å°) of berbamine loaded SLNs, Compritol® 888 ATO, phospholipon 90G and physical mixture of Compritol® 888 ATO with PEG 400 melted and solidified. The tube voltage and current were set at 45 kV and 40 mA respectively. The divergence slit and anti-scattering slit setting were set at 0.44° for the irradiation on the 10 mm specimen length. Each sample was packed in an aluminium sample holder and measured by continuous scan from 4.0084° to 49.9934°, 2θ at a step size of 0.0170° C. and scan time of 25 s.

Figure 8:
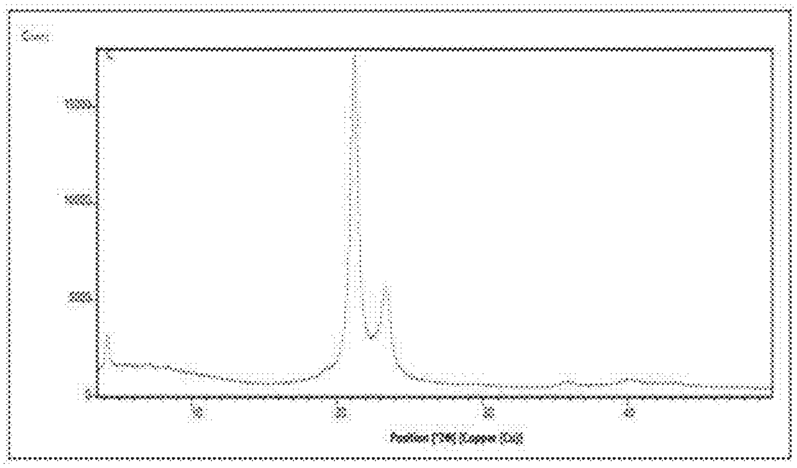
FIG. 8: illustrates PXRD of a) Compritol® 888 ATO, b) Compritol® 888 ATO melted with PEG 400, c) phospholipon 90 and d) berbamine SLNs
Figure 8:
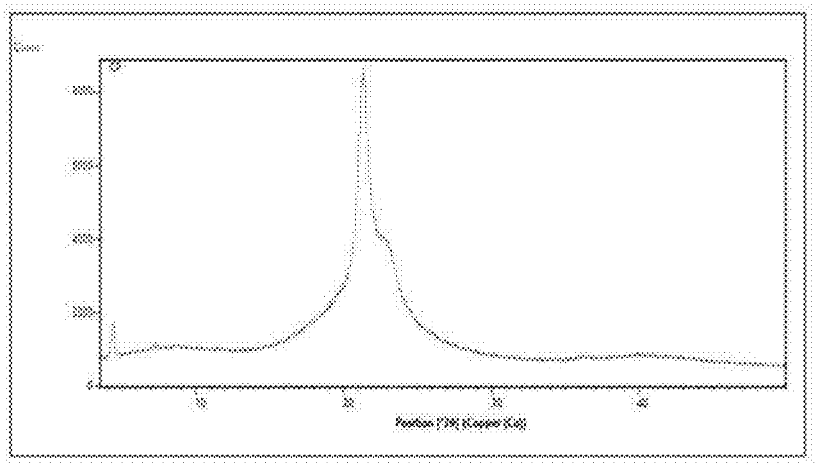
Figure 8:
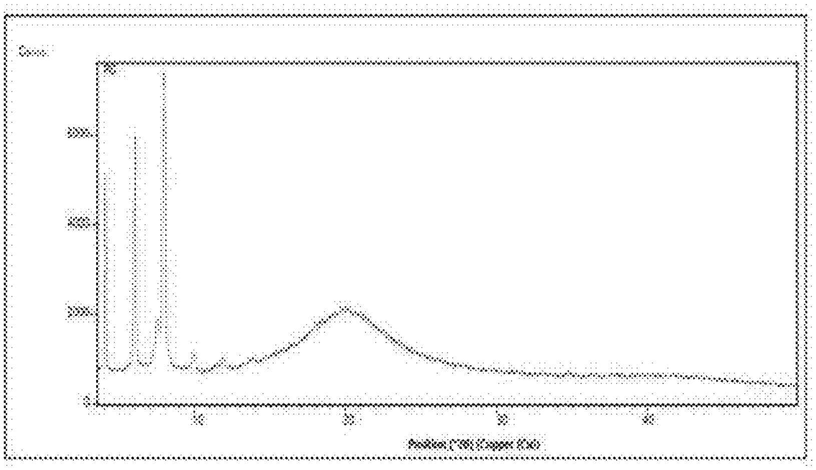
Figure 8:
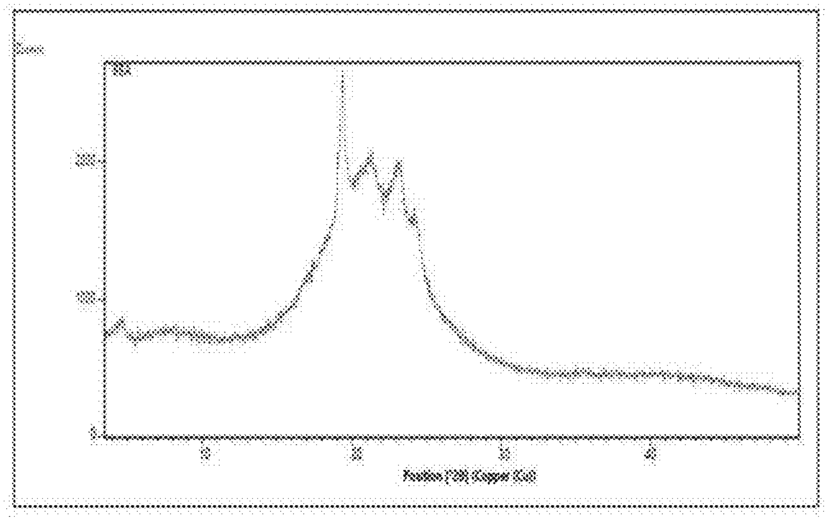

PXRD of Compritol® 888 ATO, Compritol® 888 ATO melted with PEG 400, phospholipon 90 G, berbamine loaded SLNs are shown in Figure-8. XRD pattern of Compritol® 888 ATO showed sharp peaks at 2 scattered angles 21.19 and 23.29 indicating its crystalline state. Compritol®888 ATO melted with PEG 400 showed pattern of peaks similar to that exhibited by Compritol® 888 ATO alone. This confirms the results obtained from their FTIR spectra that PEG 400 does not interact with Compritol® 888 ATO. Berbamine loaded SLNs showed broad and diffuse peaks with low intensities thus indicating its amorphous nature in the SLNs.

Example 15

Characterization of Gels

Rheological Studies

Figure 9:
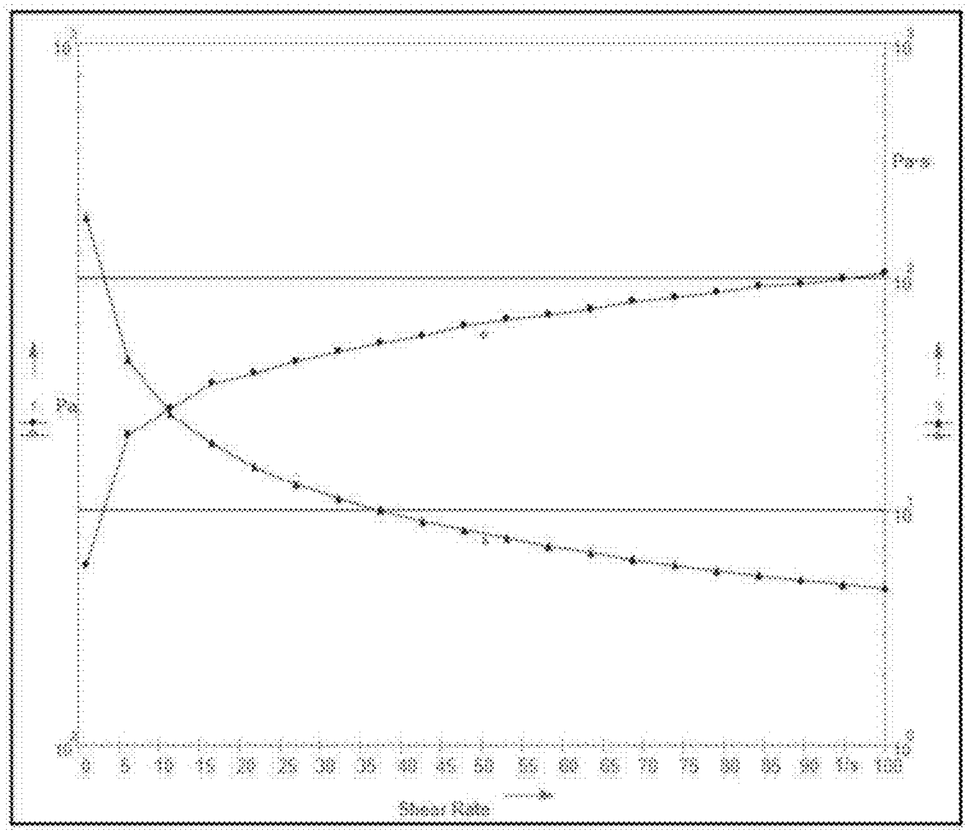
FIG. 9: illustrates rheological profile of berbamine loaded SLNs gel depicting relationship between shear rate, viscosity and shear stress.

Rheological study of the prepared berbamine loaded SLNs gel was performed using a rotational type rheometer (Rheolab QC, Anton Par GmbH, Vienna, Austria attached with a water jacket (C-LTD80/QC) for maintaining constant temperature. Data analysis was carried out using Rheoplus/32, version 3.40. ACC27 spindle geometry was used for measuring the torque as well as viscosity of the sample. Temperature was kept at 30° C. and shear rate was selected from 0 to 100 $s^{-1}$ Rheological behaviour of any formulation depicts the structural changes that occur within a system on application of shear during its processing, storage and usage. Rheological profile of the SLNs gels, berbamine loaded SLNs gel are shown in FIG. 9. It was obtained by measuring the shear rate at different levels of shear stress, initially by increasing and then by decreasing the speed of rotation of the spindle of the viscometer. The viscosity of the formulation decreased with increase in shear stress suggesting a shear thinning system. Shear thinning is a desirable property of topical gels as it facilitates ease of application. The decrease in viscosity with increasing shear rate also suggested a non-flocculated system with a very small particle size pointing towards stability of the system.

pH pH of berbamine loaded SLNs gel was measured using L1-120 pH meter (Elico, Mumbai, India).

Berbamine loaded SLNs gel showed pH in the range of 5.5 to 6.3, which is close to skin pH of 5.5.

Texture Analysis (Spreadability)

Texture profile analysis was performed to study other rheological characteristics, i.e; firmness and stickiness, of berbamine loaded SLNs gel using TTC spreadability rig fitted on Texture Analyzer™ (M/s Stable Micro Systems Ltd; UK). About 10 g of formulation was pressed to remove any air pockets (entrapped air). Excess formulation was scraped off to leave a flat test area.

Before testing, the upper cone probe (male cone) was calibrated against lower cone so that the starting point was at the same height for each test approx. 25 mm above to the lower cone. During testing, upper conical probe approached and then penetrated into sample and continued to depth 2 mm above the sample holder surfaces i.e. probe moved a distance of 23 mm from its starting point (test speed 3 mm/sec). The force encountered by the male cone to break away from the gel when starting to ascend (the point of maximum force) was measured. The value of the peak force was taken as the measurement of gel strength; the higher the value better is the strength of gel network. The area of the curve up to this point was taken as the measurement of work of shear, reflecting the work of spreadability of the sample. The negative region of the graph, produced on probe return, was a result of the weight of the sample which is lifted primarily on the upper surface of the male cone on return. This is due to back movement and hence, provides an indication of adhesion or resistance to flow off the disc. The maximum negative value is the force of adhesion for the gel and it represents the force required to extrude gel from tube. The area of the negative region of the curve was taken as work of adhesion or stickiness.

Figure 10:
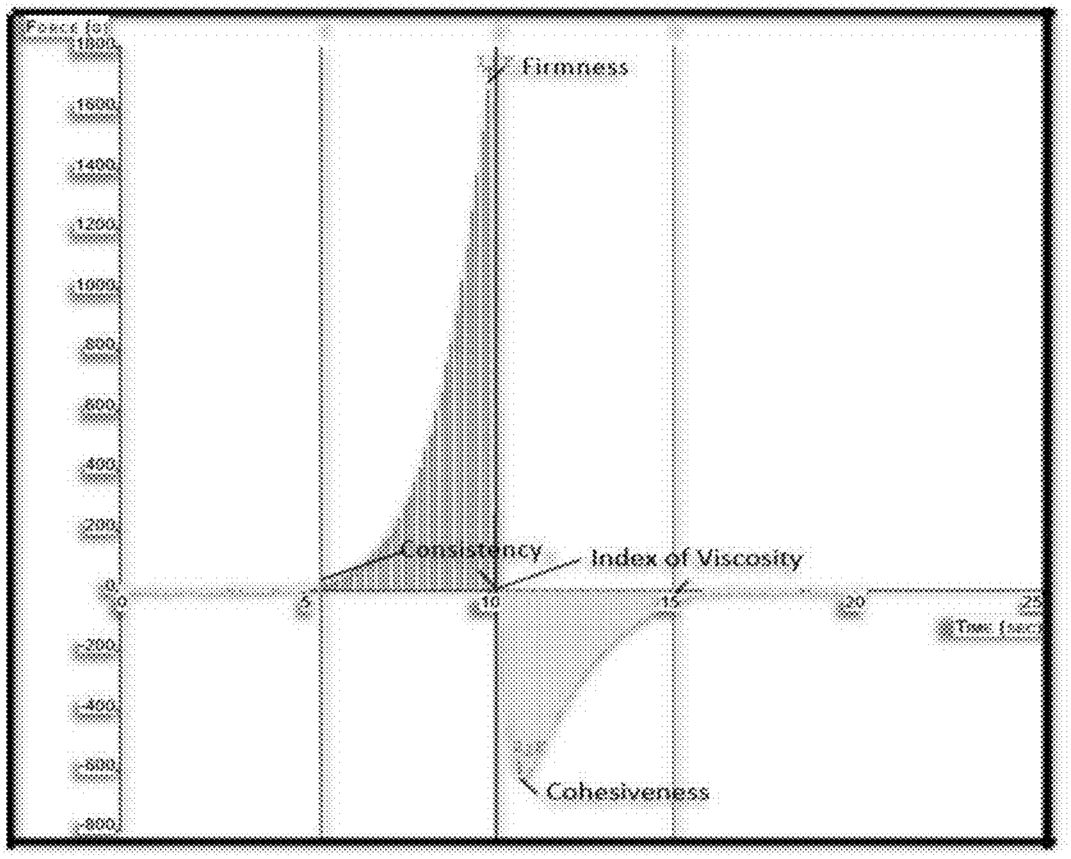
FIG. 10: illustrates texture analysis plot of berbamine loaded SLNs gel

Spreadability is one of the important factors for topical formulations and is responsible for stickiness, ease of application, extrudability from the container and overall consumer acceptability of a product. The results from texture analysis included firmness, consistency (work of shear), cohesiveness (extrusion force) and index of viscosity (work of adhesion) as shown in Table-1. It revealed that the developed formulation of berbamine loaded SLNs gel exhibited fairly good strength, ease of spreading and extrusion from container (FIG. 10). It also possessed adequate cohesiveness, which is usually essential to hold the formulation at the site of action.

TABLE 3

| Texture analysis parameters | | | | |
|---|---|---|---|---|
| Formulation | Firmness (g) | Consistency (g · sec) | Cohesiveness (g) | Index of viscosity (g · sec) |
| Berbamine loaded SLNs gel | 1680.35 | 2285.24 | −631.08 | −1382.33 |

In-Vitro Release Studies

In-vitro release studies were performed using Franz diffusion assembly. Dialysis membrane with a molecular weight cut-off of 12000-14000 Da was used after soaking in double distilled water for 12 hours. The release medium (30 mL) in each cell was maintained at 37° C. and stirred throughout the time of experiment.

For berbamine loaded SLNs gel and free berbamine gel in-vitro release studies ethanol:phosphate buffer pH 6.8 (30:70) was taken as release medium. The dialysis membrane was loaded with 500 mg of SLNs gel. Aliquots of 0.5 mL were withdrawn at different time intervals for 120 h and replenished with same volume of release medium. The collected samples were suitably diluted and analysed by UV-visible spectrophotometer. For free berbamine gel, dialysis membrane was loaded with 500 mg of berbamine gel instead of SLNs gel and similar procedure was followed as for berbamine loaded SLNs gel.

Figure 11:
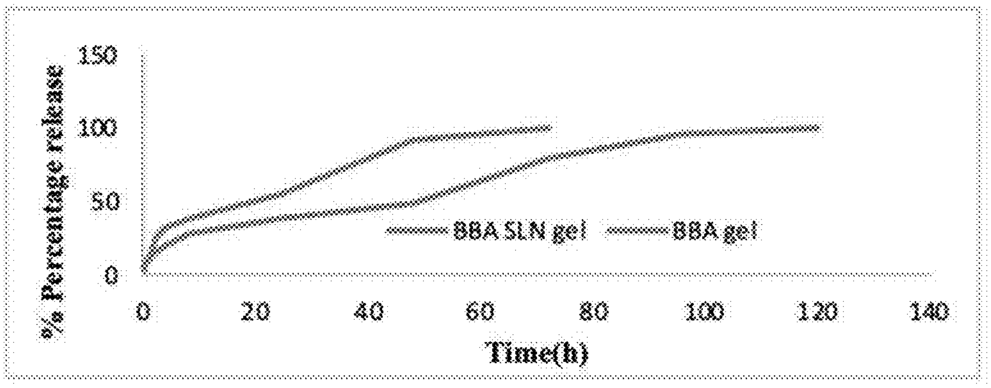
FIG. 11: illustrates in vitro release of berbamine loaded SLNs gel (BBA SLNs) and berbamine gel (BBA)

In vitro release profile of berbamine loaded SLNs gel at 37±0.5° C. is shown in FIG. 11. Berbamine loaded SLNs gel showed 100% release of the drug in 120 hours, whereas, berbamine Blank gel showed 100% release in 72 hours. From the release studies it can be inferred that due to formation of solid lipid nanoparticles release span of berbamine has been increased which is beneficial for prolonged pharmacological activity.

Antimicrobial Activity

Berbamine was tested for a panel of bacterial strains including *Pseudomonas aeruginosa* (ATCC 27853), *Acinetobacter baumannii* (ATCC 19606), *Staphylococcus aureus* (ATCC 29213) and clinical isolates of *Klebsiella pneumoniae, Staphylococcus epidermidis, Staphylococcus hemolyticus* and *Burkholderia cepacia* complex using serial dilution method. Ceftazidime was used as the standard antibiotic for validating the protocol. The minimum inhibitory concentrations (MIC) against all seven strains are shown in Table 4.

TABLE 4

Minimum inhibitory concentrations (MIC) of berbamine against different bacterial strains.

| Bacterial strain | MIC (μg/mL) |
|---|---|
| *Staphylococcus aureus* | 256 |
| *Staphylococcus epidermidis* | 128 |
| *Staphylococcus hemolyticus* | 128 |
| *Acinetobacter baumannii* | 256 |
| *Burkholderia cepacia complex* | — |
| *Klebsiella pneumonia* | >4096 |
| *Pseudomonas aeruginosa* | — |

Berbamine was also tested for its activity against carbapenem resistant *Acinetobacter baumannii* (CRAB) strain (C-5020). The combination of meropenem and berbamine was also evaluated against *Acinetobacter baumannii* (ATCC 19606) and carbapenem resistant *Acinetobacter baumannii* (CRAB) strain (C-5020). The checkerboard method was performed in duplicate and the fractional inhibitory concentration index (FICI) of around 0.2 which is less than 0.5 showed there is synergy between meropenem and berbamine for carbapenem resistant *Acinetobacter baumannii* (CRAB) strain (C-5020).

Pharmacodynamic Activity in Animals

Excision Diabetic Wound Model

Figure 12:
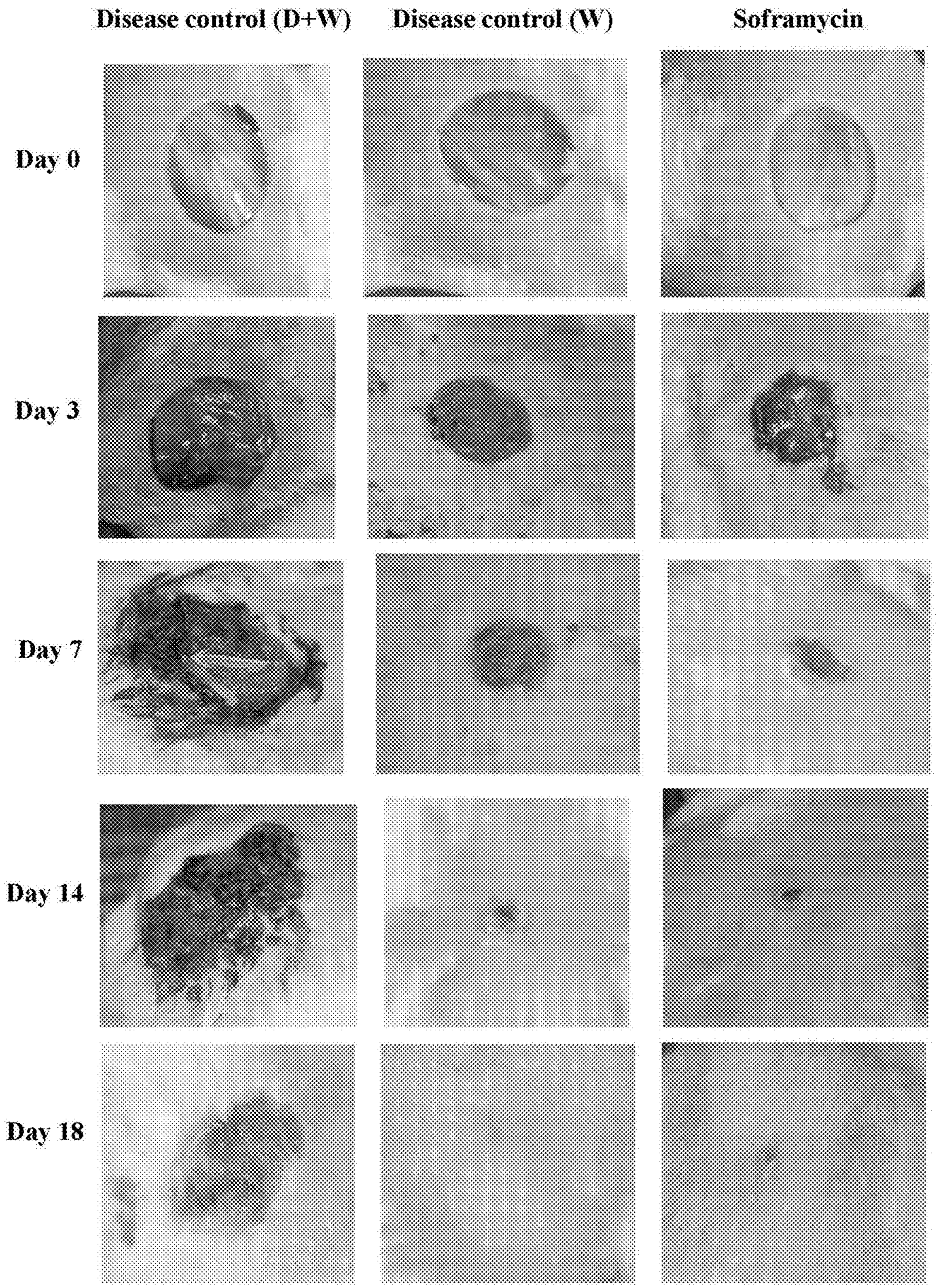
FIG. 12: illustrates representative images of the excision diabetic wound model for different groups on different days.
Figure 13:
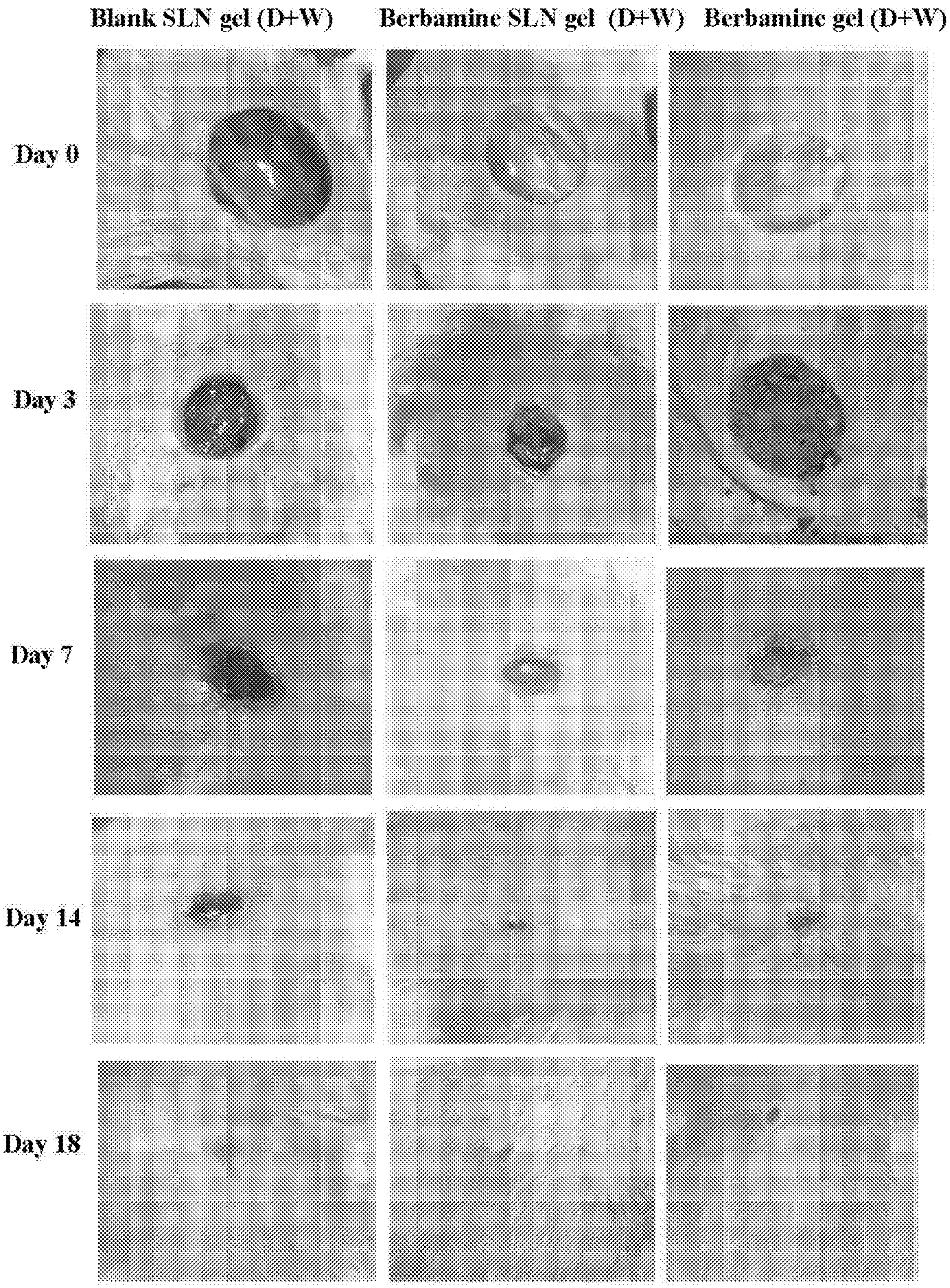
FIG. 13: illustrates representative images of the excision diabetic wound model for different groups on different days

The in vivo healing potential of berbamine loaded SLNs gel and berbamine gel was assessed in comparison to marketed product (Soframycin:1% w/w) using diabetic excision wound model. Representative images of the reduction in the excision wound size with the passage of time (at 0, 3, 7, 14, 18 days) are depicted in FIGS. 12-13. In disease control group typical infectious diabetic wounds and delayed pattern of wound healing was observed, whereas, in control (wound only), partial healing was observed. The healing of wounds during the initial 0 to 3 days was found to be faster in berbamine loaded SLNs treated group. This is of significance as it would be helpful in preventing bacterial infections of the wounds. At the end of treatment wound healing potential of berbamine loaded SLNs gel versus berbamine gel were comparable as the berbamine loaded SLNs gel showed 98% wound healing in comparison to 93% wound healing in berbamine gel. The effect of healing was observed to be better than the standard drug which showed 91% of wound healing. Biochemical estimations and histopathology studies were also performed to study the healing process.

TABLE 5

| Wound healing activity Diameter of wound (mm) | | | | | |
|---|---|---|---|---|---|
| Day | Berbamine SLN gel | Berbamine gel | Blank SLN gel | Marketed standard | Disease control |
| 0 | 5.2 ± 0.08 (0) | 5.1 ± 0.11 (0) | 5.0 ± 0.08 (0) | 5.2 ± 0.09 (0) | 5.1 ± 0.1 |
| 3 | 3.8 ± 0.05 (26.92) | 4.2 ± 0.08 (17.64) | 4.9 ± 0.05 (2) | 4.75 ± 0.07 (8.65) | 5.8 ± 0.11 |
| 7 | 2.56 ± 0.045 (50.76) | 2.86 ± 0.05 (43.92) | 4 ± 0.07 (20) | 3.13 ± 0.06 (37.5) | 8 ± 0.12 |
| 14 | 0.65 ± 0.03 (87.5) | 0.78 ± 0.04 (84.70) | 1.37 ± 0.05 (72.5) | 0.85 ± 0.03 (83.65) | 10 ± 0.18 |
| 18 | 0.12 ± 0.02 (97.69) | 0.35 ± 0.04 (93.13) | 1 ± 0.03 (80) | 0.45 ± 0.02 (91.34) | 7.5 ± 0.15 |

*the Values in Parenthesis Indicates Percent Wound Healing

Incision Diabetic Wound Model

Figure 14:
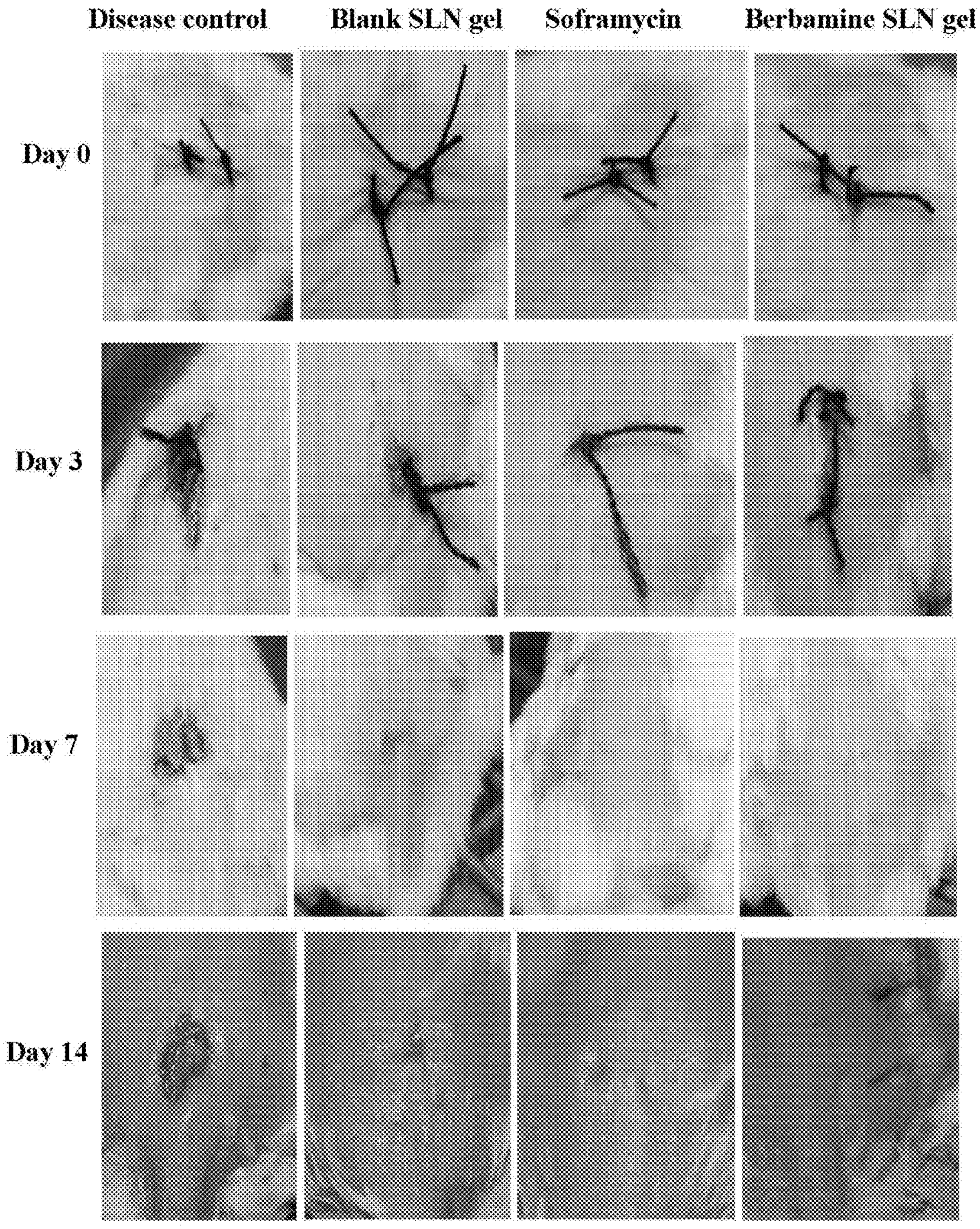
FIG. 14: illustrates representative images of the incision diabetic wound model for different groups on different days.

The in vivo healing potential of the berbamine loaded SLNs gels was assessed in comparison with the commercial product (Soframycin: 1% w/w) using incision diabetic wound model for 14 days. The representative images of incision wound healing with passage of time (at 0, 3, 7, 14 days) are shown in FIG. 14. The disease control and blank gel demonstrated delayed healing process compared to other groups, whereas, faster re-modelling was observed in groups treated with berbamine loaded SLNs gel and marketed standard. Biochemical estimations and histopathology studies were performed to study the healing process.

Biochemical Investigations

Protein Estimation

Protein plays central role in wound healing through the production of collagen. Hence an increase in protein content confirms the healing of wounds.

Figure 15:
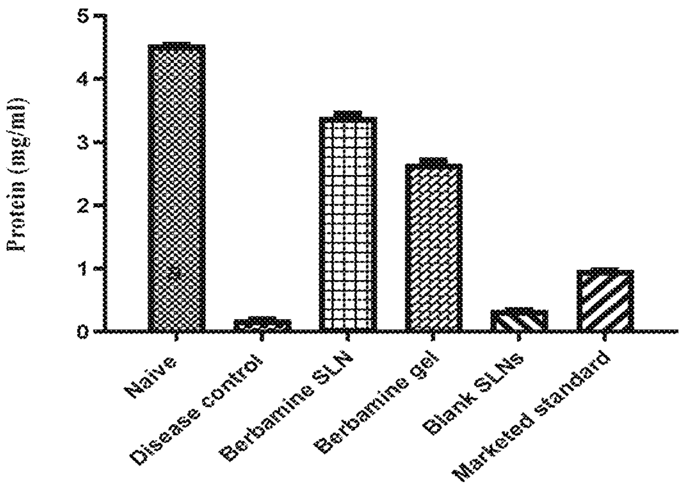
FIG. 15: illustrates protein content during wound healing (diabetic wound excision model).

Protein content was significantly decreased in disease control as compared to naive group. All treatment groups in diabetic wound excision model showed significantly different activity from disease control group as depicted in FIG. 15. Protein content was increased by 85.35% ($p<0.05$) for berbamine gel and 115.4% in case of berbamine loaded SLNs gel and 28% for marketed standard ($p<0.05$) as compared with disease control group. Blank gel showed protein content increased by 5.2% as compared to disease control group.

Figure 16:
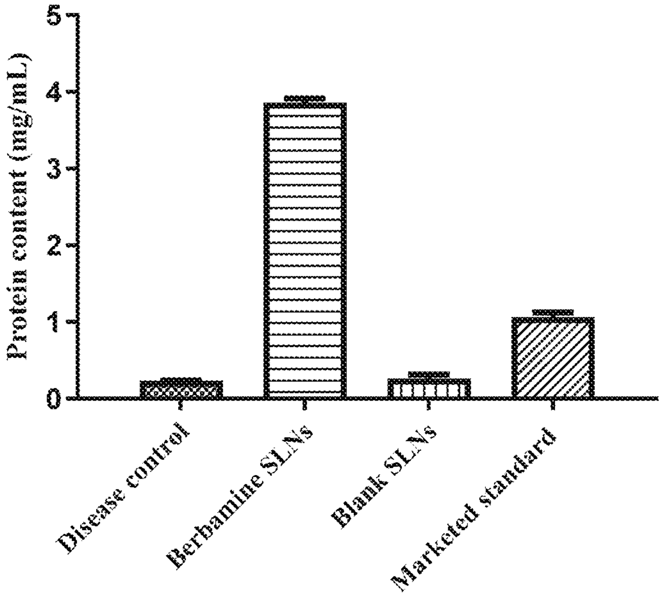
FIG. 16: illustrates protein content during wound healing (diabetic wound incision model).

In diabetic wound incision model treatment groups showed significantly different activity from disease control group as depicted in FIG. 16. Protein content was increased by 74.66% in case of berbamine loaded SLNs gel and 17.07% for marketed standard ($p<0.05$) as compared with disease control group.

Blank gel showed protein content increased by 0.62% as compared to disease control group.

Acetylcholinesterase Inhibitory Activity

Acetylcholine has role in wound epithelialization. Acetylcholinesterase (AChE) is responsible for breakdown of acetylcholine so, decrease in levels of acetylcholinesterase confirms healing of wounds.

Figure 17:
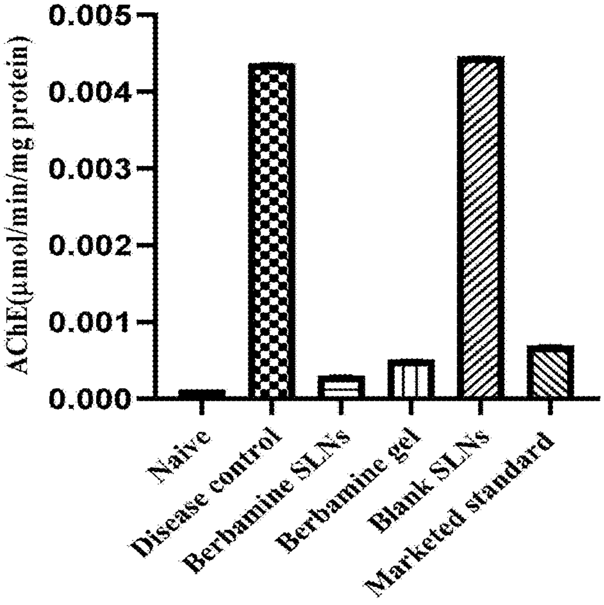
FIG. 17: illustrates AChE activity during wound healing (diabetic wound excision model).

AChE was significantly increased in disease control as compared to naïve group. All treatment groups in diabetic wound excision model showed significantly different activity from disease control group as depicted in FIG. 17. AChE was decreased by 23.49% in case of berbamine loaded SLNs gel, 22.29% for berbamine gel and 21.22% for marketed standard ($p<0.05$) as compared with disease control group. Blank SLNs gel showed AChE decreased by 0.5% as compared to disease control group.

Figure 18:
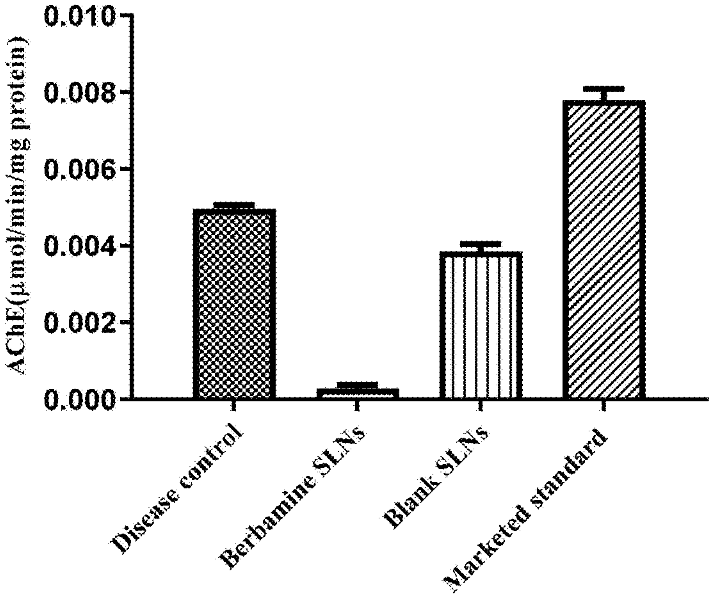
FIG. 18: illustrates AChE activity during wound healing (diabetic wound incision model).

All treatment groups in diabetic wound incision model showed significantly different activity from disease control group as depicted in FIG. 18. AChE was decreased by 28.01% in case of berbamine loaded SLNs gel and 26.95% for marketed standard ($p<0.05$) as compared with disease control group.

Blank gel showed AChE decreased by 6% as compared to disease control group. Among all treatment groups berbamine loaded SLNs gel produced greater decrease in AChE and was significantly ($p<0.05$) more than the marketed standard.

Measurement of Free Radical and Antioxidants Level

Free radicals (lipid peroxidation), antioxidants (catalase, superoxide dismutase and reduced glutathione) imbalance in free radical generation and antioxidants induce oxidative stress, tissue damage and delayed wound healing. So, decrease in free radicals and increase in antioxidants content helps in chronic wound healing.

Figure 19:
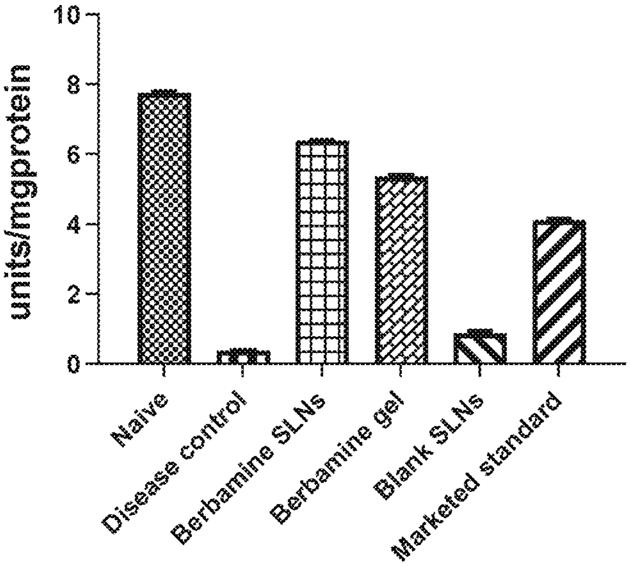
FIG. 19: illustrates SOD levels during wound healing (diabetic wound excision model).
Figure 20:
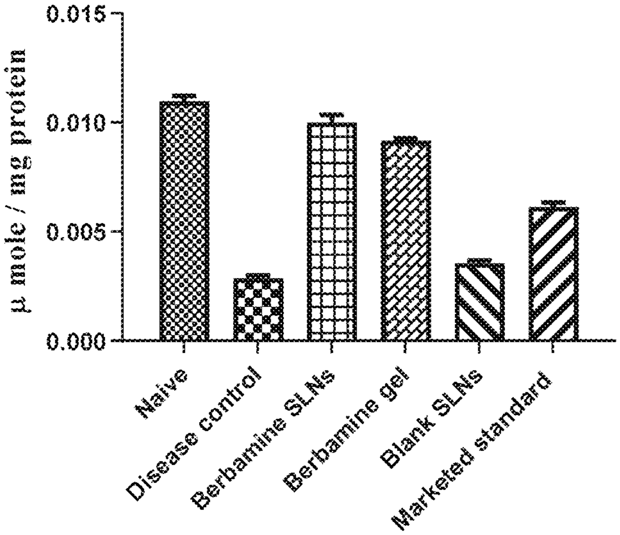
FIG. 20: illustrates GSH levels during wound healing (diabetic wound excision model).
Figure 21:
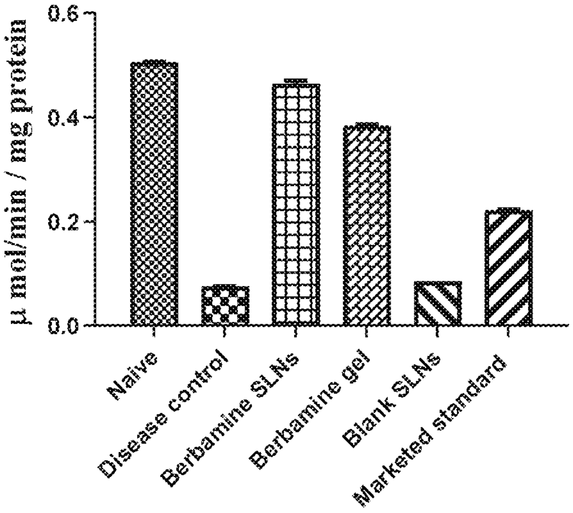
FIG. 21: illustrates catalase levels during wound healing (diabetic wound excision model).

The superoxide dismutase (SOD), reduced glutathione (GSH) and catalase levels were significantly decreased in disease control group in comparison to naïve group. All treatment groups in diabetic wound excision model showed significantly different activity from disease control group as depicted in FIGS. 19-21.

SOD was increased by 168% in case of berbamine loaded SLNs gel and 105.3% for marketed standard ($p<0.05$) as compared with disease control group. Berbamine loaded SLNs gel also showed significantly different SOD levels versus berbamine gel by 28.69%. In case of berbamine gel, an increase by 140.2% was observed while in and blank gel an increase by 14.10% was observed as compared to disease control group.

GSH was increased by 37.18% in case of berbamine loaded SLNs gel and 17.02% for marketed standard ($p<0.05$) as compared with disease control group. In case of berbamine gel, the increase was by 32.84% and blank gel showed increase by 3.5% as compared to disease control group.

Catalase was increased by 161% in case of berbamine loaded SLNs gel and 49.7% for marketed standard ($p<0.05$) as compared with disease control group. Berbamine gel showed increase by 127.7% and blank gel showed increase by 6.85% compared to disease control group. Berbamine loaded SLNs gel versus berbamine gel showed significantly different catalase levels. Berbamine loaded SLNs gel increased catalase by 33.34% as compared to berbamine gel.

Among all treatment groups berbamine loaded SLNs gel produced increase in SOD, GSH and catalase levels significantly ($p<0.05$) more than the Blank gel as well as marketed standard.

Figure 22:
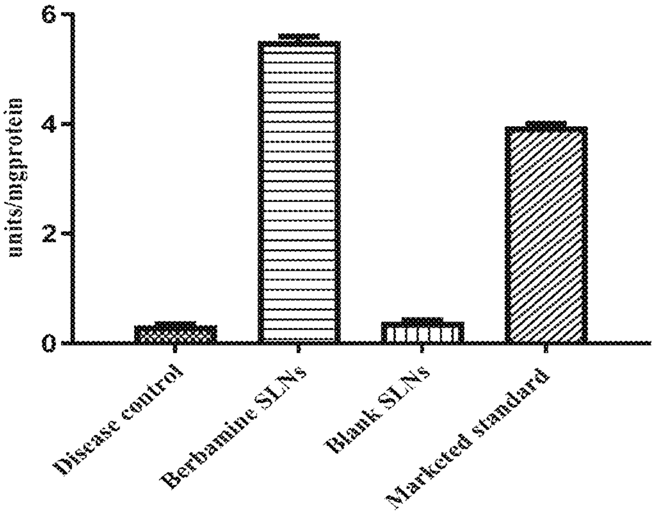
FIG. 22: illustrates SOD levels during wound healing (diabetic wound incision model).
Figure 23:
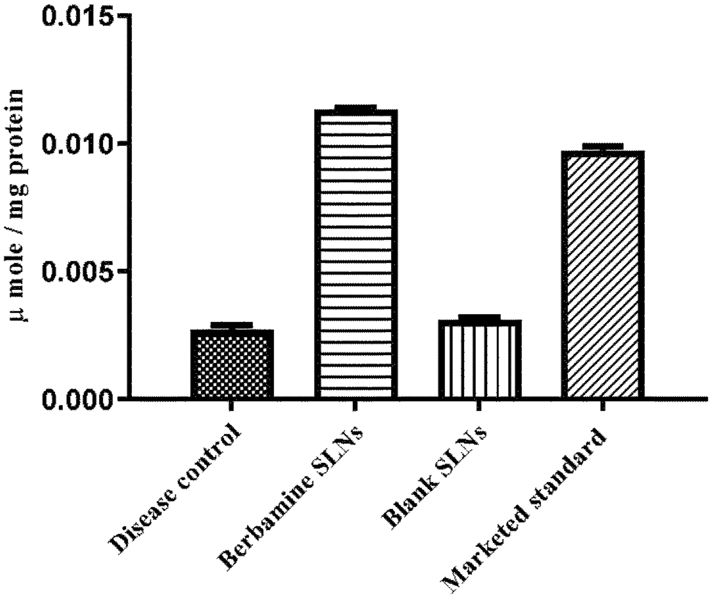
FIG. 23: illustrates GSH levels during wound healing (diabetic wound incision model).
Figure 24:
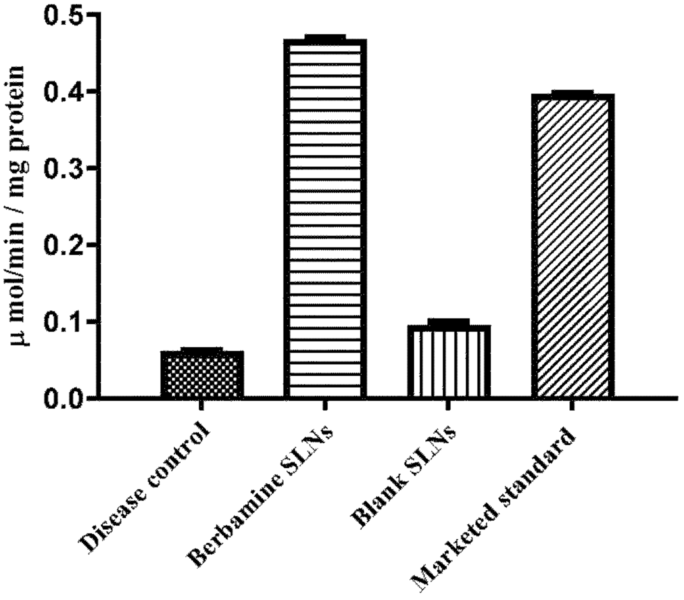
FIG. 24: illustrates catalase levels during wound healing (diabetic wound incision model).

In case of diabetic wound incision model, all treatment groups showed significantly different activity from disease control group as depicted in FIGS. 22-24. SOD was increased by 93.04% in case of berbamine loaded SLNs gel and 65.01% for marketed standard ($p<0.05$) as compared with disease control group. In case of blank gel, increase by 1.12% as compared to disease control group was observed.

GSH was increased by 44.12% in case of berbamine loaded SLNs gel and 35.91% for marketed standard ($p<0.05$) as compared with disease control group. In case of blank gel, increase by 2.05% compared to disease control group was observed. Catalase was increased by 128.7% in case of berbamine loaded SLNs gel and 105.9% for marketed standard ($p<0.05$) as compared with disease control group. In case of blank gel increase by 6.85% compared to disease control group was observed.

Among all treatment groups berbamine loaded SLNs gel produced increase in SOD, GSH and catalase levels significantly ($p<0.05$) in diabetic wound incision model more than the marketed standard.

Figure 25:
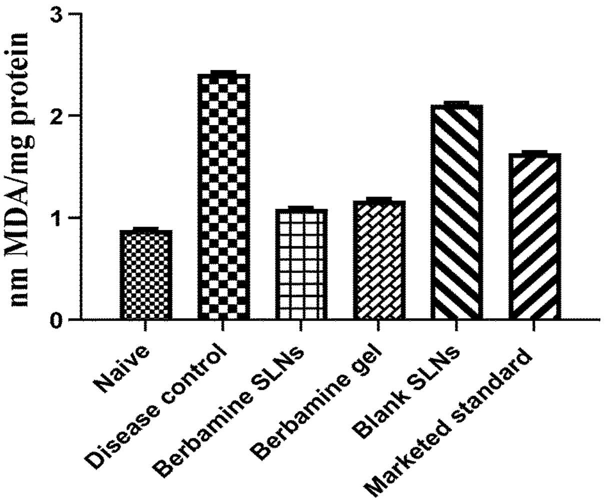
FIG. 25: illustrates LPO levels during wound healing (diabetic wound excision model).

The lipid peroxidation (LPO) levels were significantly increased in disease control group in comparison to naïve group. All treatment groups in diabetic wound excision model showed significantly different activity from disease control group as depicted in Figure-25. LPO level was decreased by 83.8% in case of berbamine loaded SLNs gel, 49.15% for marketed standard, 78.62% for berbamine gel and 19.22% for blank gel as compared to disease control group. Berbamine loaded SLNs gel showed significantly different activity than berbamine gel as LPO was decreased by 5.18% in berbamine loaded SLNs gel in comparison to berbamine gel.

Among all treatment groups berbamine loaded SLNs gel produced decrease in LPO levels significantly ($p<0.05$) more than the marketed standard.

Figure 26:
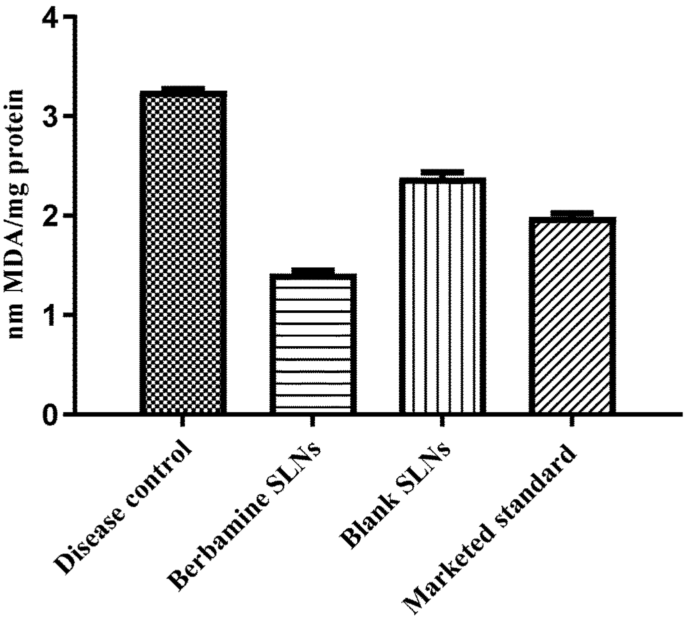
FIG. 26: illustrates LPO levels during wound healing (diabetic wound incision model).

In case of diabetic wound incision model LPO level was decreased by 42.50% in case of berbamine loaded SLNs gel and 29.3% for marketed standard ($p<0.05$) as compared with disease control group as shown in FIG. 26. In case of blank gel, LPO level showed decrease by 19.22% as compared to disease control group. Among all treatment groups berbamine loaded SLNs gel produced decrease in LPO levels significantly ($p<0.05$) more than the marketed standard.

Histopathological Studies

Effect of Wound Healing on Skin Tissue in Diabetic Wound Excision Model

Figure 27:
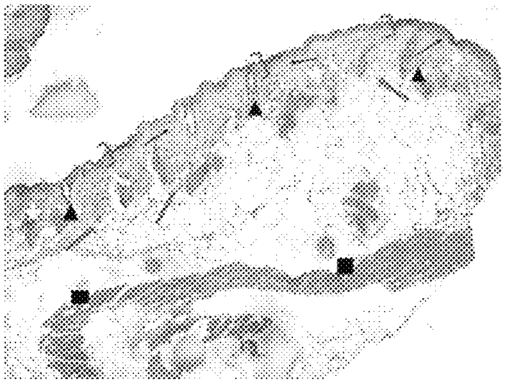
FIG. 27: illustrates the photomicrographs of histopathological study of skin sections after staining with haematoxylin eosin in different treatment and control group for excision wound healing model.
Figure 27:
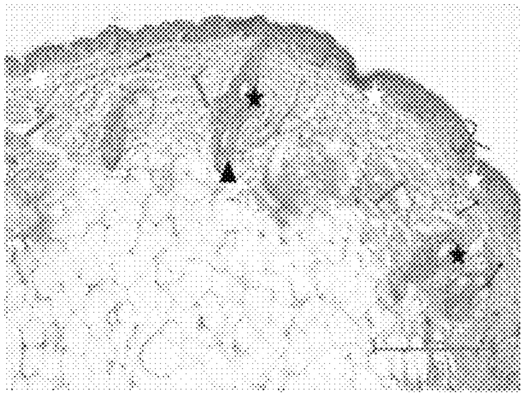
Figure 27:
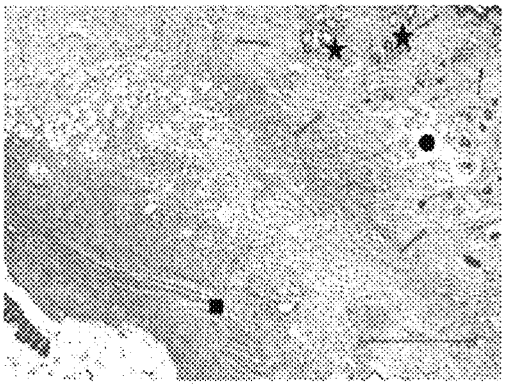
Figure 27:
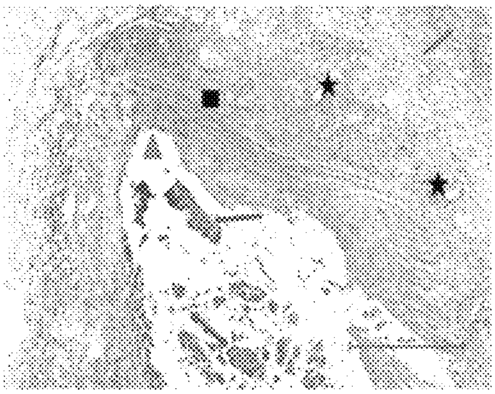
Figure 27:
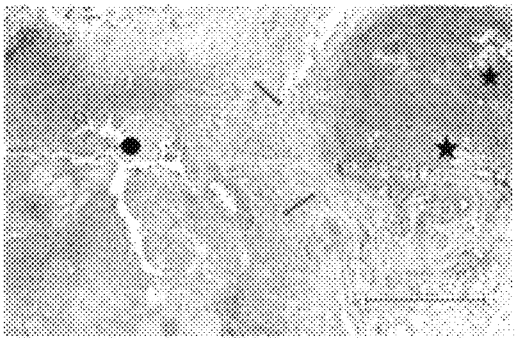
Figure 27:
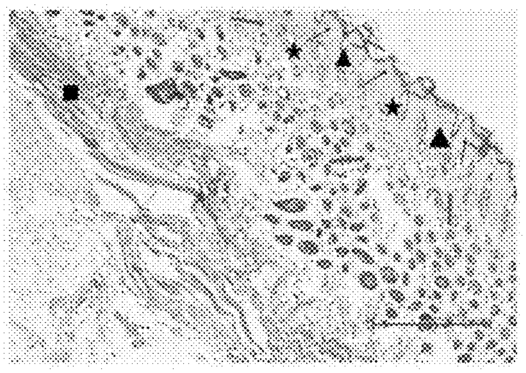
Figure 27:
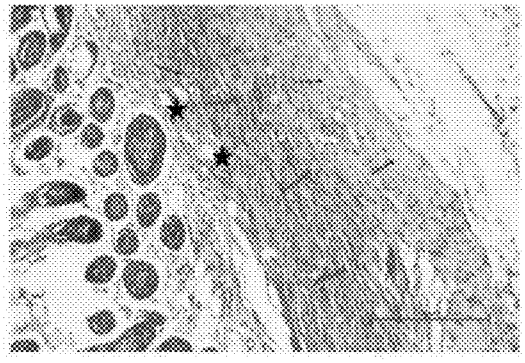
Figure 27:
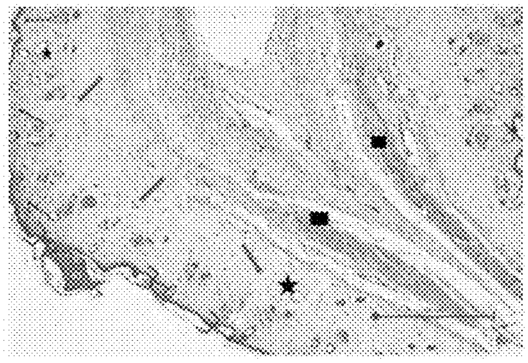
Figure 27:
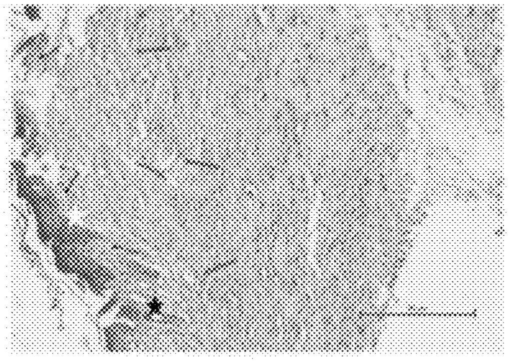
Figure 27:
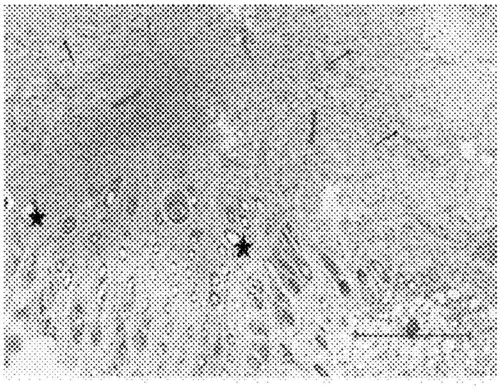
Figure 27:
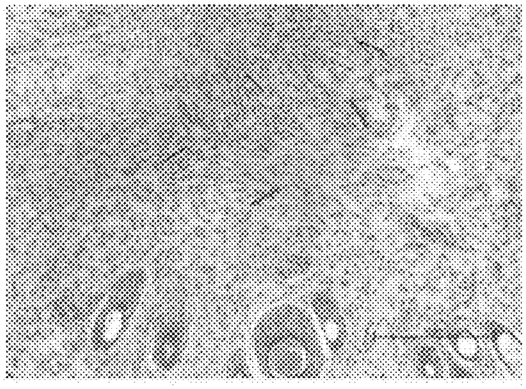
Figure 27:
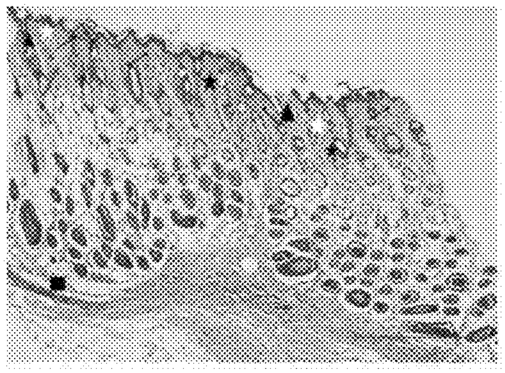
Figure 27:
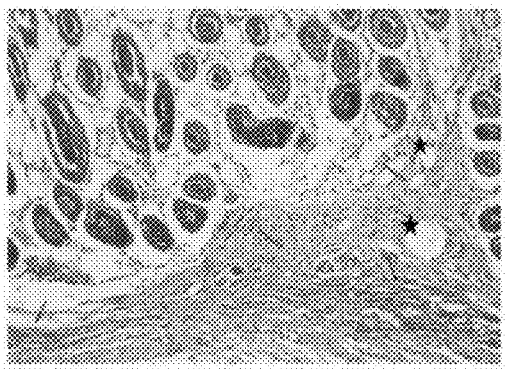

Hematoxylin and eosin-stained sections of skin are shown in FIG. 27. Histopathological study of naïve group showed normal skin from epidermis to subcutaneous tissue. Epidermis was well organized in multiple cell layers, along with numerous dermal papillae. Presence of bundles of collagen fibers and dermal appendages was also observed. However, in case of disease control eosinophil necrotic tissue, abscess cavity containing pus was observed. Collagen fibers were dispersed and no presence of skin appendages was seen whereas, in case of blank SLNs active inflammation with signs of early healing was observed.

In case of treatment groups, berbamine loaded SLNs gel and marketed standard, a partial or full healing of skin was observed as compared to other groups.

In skin section of berbamine loaded SLNs gel normal skin was observed with dense fibroblasts and mature fibrous cells. Collagen fibers were organized in large bundles and presence of dermal appendages was also observed.

In case of marketed standard group epidermis and dermis were fairly normal and mild edema in the deeper dermis was observed.

So, in conclusion excellent healing was observed in berbamine loaded SLNs gel group as at the end of treatment normal skin was observed in comparison to other treatment groups. Disease control showed the condition of typical diabetic wounds with infectious abscess cavity containing pus and delayed wound healing pattern.

Effect of Wound Healing on Skin Tissue in Diabetic Wound Incision Model

Figure 28:
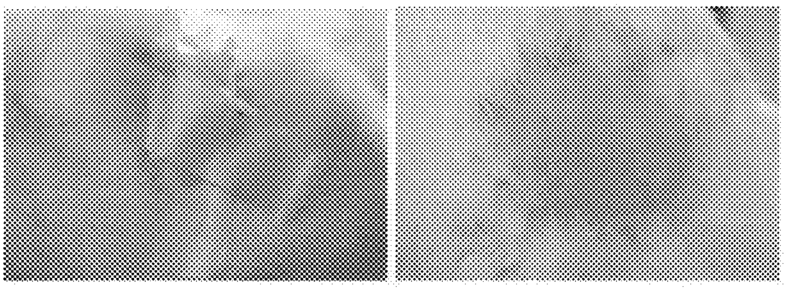
FIG. 28: illustrates photographs of rabbit before and after application (72 h) of berbamine loaded SLNs.

Hematoxylin and eosin-stained sections of skin for incision model are shown in FIG. 28. Histopathological study of disease control group showed irregular epidermis with focal hyperplasia, with fair amount of chronic inflammatory cells and fibroblasts in the dermis. In deep subcutaneous tissue was seen edema with fibroblast proliferation and inflammation. In case of blank SLNs gel linear healing scar from the epidermis was seen along with presence of degenerating necrotic tissue and localized foci of hyperplasia was also observed.

In case of treatment groups berbamine loaded SLNs gel and marketed standard drug there were signs of healing of tissue. In berbamine loaded SLNs gel fairly normal skin was observed. The healed area showed collagenous scar in the dermis and early healing of hair follicles. In case of marketed standard hair follicles were normal and early fibrosis in the subcutaneous tissue beneath muscle layer was observed.

Example 16

Toxicity Studies:

Acute dermal irritation studies were conducted as per OECD Guidelines 404. The scores for dermal irritation study are compiled in table below. Zero score value clearly demonstrates a non-irritant nature of the developed formulation when applied to dermal tissues, and hence is concluded to be safe for topical application. FIG. 28 shows the test animal before and after the application of formulation.

TABLE 6

| Scores of acute dermal irritation study of berbamine loaded SLNs in rabbits | | | | | | | | | | | | | | | |
|---|---|---|---|---|---|---|---|---|---|---|---|---|---|---|---|
| Tissue | Rabbit 1 | | | | | Rabbit 2 | | | | | Rabbit 3 | | | | |
| reaction | 0 h | 1 h | 24 h | 48 h | 72 h | 0 h | 1 h | 24 h | 48 h | 72 h | 0 h | 1 h | 24 h | 48 h | 72 h | Score |
| Erythema | 0 | 0 | 0 | 0 | 0 | 0 | 0 | 0 | 0 | 0 | 0 | 0 | 0 | 0 | 0 | 0/60 |
| Oedema | 0 | 0 | 0 | 0 | 0 | 0 | 0 | 0 | 0 | 0 | 0 | 0 | 0 | 0 | 0 | 0/60 |
| Total Score | | | | | | | | | | | | | | | | 0/120 |

The invention claimed is:

1. A process for preparing solid lipid nanoparticles of berbamine, the process comprising:
   i) preparing a lipid phase by melting one or more lipids at a temperature at least equal to a melting point of the one or more lipids, wherein the one or more lipids are selected from the group consisting of glycerides and fatty acids;
   ii) separately preparing an aqueous phase by admixing at least one surfactant, at least one co-surfactant and water followed by heating at a temperature at least equal to the melting point of the one or more lipids;
   iii) dissolving berbamine in the aqueous phase to obtain a berbamine containing aqueous phase and maintaining at a pH in a range of 6-8.5, or dissolving berbamine in the lipid phase to obtain a berbamine containing lipid phase and maintaining at a pH in a range of 6-8.5;
   iv) adding the berbamine containing lipid phase to the aqueous phase of step (ii) or adding the berbamine containing aqueous phase to the lipid phase of step (i), and mixing at a speed in a range of 5,000-20,000 rpm for a period in a range of 5-30 min to obtain a primary coarse emulsion; and
   v) subjecting the primary coarse emulsion to two to six cycles of homogenization at a pressure in a range of 500 to 1200 bars to obtain the solid lipid nanoparticles of berbamine.

2. A process for preparing solid lipid nanoparticles of berbamine, the process comprising:
   i) preparing a lipid phase by melting one or more lipids at a temperature at least equal to a melting point of the one or more lipids, wherein the one or more lipids are selected from the group consisting of glycerides and fatty acids;
   ii) separately preparing an aqueous phase by admixing at least one surfactant, at least one co-surfactant and water followed by heating at a temperature at least equal to the melting point of the one or more lipids;
   iii) dissolving berbamine in polyethylene glycol 400 (PEG 400) and adding the dissolved berbamine to the aqueous phase to obtain a solution, and maintaining the solution at a pH in a range of 7.5-8.5;
   iv) adding the lipid phase of step (i) to the solution of step (iii), and mixing at a speed in a range of 5,000-20,000 rpm for a period in a range of 5-30 min to obtain a primary coarse emulsion; and
   v) subjecting the primary coarse emulsion to two to six cycles of homogenization at a pressure in a range of 500 to 1200 bars to obtain the solid lipid nanoparticles of berbamine.

3. A process for preparing solid lipid nanoparticles of berbamine, the process comprising:
   i) preparing a lipid phase by melting one or more lipids at a temperature at least equal to a melting point of the one or more lipids, wherein the one or more lipids are selected from the group consisting of glycerides and fatty acids;
   ii) separately preparing an aqueous phase by admixing at least one surfactant, at least one co-surfactant and water followed by heating at a temperature at least equal to the melting point of the one or more lipids;
   iii) dissolving berbamine in polyethylene glycol 400 (PEG 400) and adding the dissolved berbamine to the lipid phase to obtain a solution, and maintaining the solution at a pH in a range of 6-7;
   iv) adding the solution of step (iii) to the aqueous phase of step (ii), and mixing at a speed in a range of 5,000-20,000 rpm for a period in a range of 5-30 min to obtain a primary coarse emulsion; and
   v) subjecting the primary coarse emulsion to two to six cycles of homogenization at a pressure in a range of 500 to 1200 bars to obtain the solid lipid nanoparticles of berbamine.

4. The process as claimed in claim 1, wherein the process comprises dissolving the berbamine in an emulsifier before step (iii).

5. The process as claimed in claim 4, wherein the emulsifier is selected from the group consisting of polyethylene glycol (PEG), polyvinylpyrrolidone (PVP), polyvinyl alcohol (PVA), glycerol, diethylene glycol monoethyl ether, glyceryl monocaprylocaprate, propylene glycol diesters of caprylic and capric acids, medium-chain triglycerides of capric and caprylic acid, PEG esters of fatty acids and glycerides, hydrogenated vegetable glycerides, glyceryl citrate, glyceryl lactate, glyceryl linoleate, glyceryl oleate, polyglyceryl-4-cocoate, polyglyceryl-3-caprate and caprylate, polypropylene glycol, and propylene glycol.

6. The process as claimed in claim 1, wherein the at least one surfactant is present in a concentration in a range of 2-10% (w/w).

7. The process as claimed in claim 1, wherein the glycerides are selected from the group consisting of mono-glycerides, di-glycerides, tri-glycerides, and mixtures thereof.

8. The process as claimed in claim 1, wherein the glycerides are selected from the group consisting of glyceryl behenate, tricaprin, trilaurin, trimyristin, tripalmitin, tristearin, and precirol.

9. The process as claimed in claim 1, wherein the fatty acids are selected from the group consisting of saturated C4-C28 fatty acids, and unsaturated C4-C28 fatty acids.

10. The process as claimed in claim 1, wherein the fatty acids are selected from the group consisting of stearic acid, lauric acid, palmitic acid, myristic acid, and capric acid.

11. The process as claimed in claim 1, wherein the at least one surfactant is selected from the group consisting of ethylene oxide copolymers, propylene oxide copolymers, poloxamers, sorbitan ethylene oxide copolymers, sorbitan esters, alkylaryl polyether alcohol polymers, bile salts, gemini surfactants, alcohols, diethylene glycol monoethyl ethers, propanediol, alkyl polyglucosides, fatty acids, fatty alcohols, and mixtures thereof.

12. The process as claimed in claim 1, wherein the at least one co-surfactant is selected from the group consisting of soy lecithin, egg lecithin, phosphatidylcholine, cholate, glycocholate, taurocholate, taurodeoxycholate, and mixtures thereof.

13. The process for preparing solid lipid nanoparticles of berbamine as claimed in claim 1, wherein a berbamine content is in a range of 0.5-10% w/w with respect to the aqueous dispersion of the solid lipid nanoparticles, and is in a range of 12-50% w/w with respect to the lipid dispersion of the solid lipid nanoparticles.

14. The process for preparing solid lipid nanoparticles of berbamine as claimed in claim 1, wherein an entrapment efficiency of berbamine in the solid lipid nanoparticles is more than 90%.

15. Solid lipid nanoparticles of berbamine as prepared by the process as claimed in claim 1, wherein the solid lipid nanoparticles comprises:

a. a lipid phase comprising a mixture of lipids selected from the group consisting of glycerides and fatty acids; and b. an aqueous phase comprising water, at least one surfactant and, at least one co-surfactant, wherein berbamine is entrapped in the lipid phase and is present in a solubilised form in the aqueous phase, wherein berbamine in the lipid phase is at equilibrium with berbamine in the aqueous phase.

16. The solid lipid nanoparticles of berbamine as claimed in claim 15, wherein the solid lipid nanoparticles of berbamine have a particle size in a range of 50-500 nm.

17. The solid lipid nanoparticles of berbamine as claimed in claim 15, wherein the solid lipid nanoparticles of berbamine have a spherical shape.

18. The solid lipid nanoparticles of berbamine as claimed in claim 15 exhibit antimicrobial and anti-infective properties against bacterial strains, including drug-resistant strains, and promote wound healing in a subject, including subjects with diabetes and diabetes-associated complications.

19. The solid lipid nanoparticles of berbamine as claimed in claim 15 are a dispersion, a gel, a hydrogel, an organogel, a syrup, a paste, a cream, a liquid wash, facewash, mouthwash, oral rinse, an ointment, nasal drops or nasal sprays, ear drops, an aerosol spray, a powder, an orthotic aid, liquid formulations, a facemask, a film, an implant, a tablet, lozenges, capsules, suppositories, pessaries, a patch, and gummies, and are adapted for administration via one or more of oral, parenteral, dental, buccal, ocular, intranasal, vaginal, rectal, otic, transdermal, and topical delivery routes.

20. The solid lipid nanoparticles of berbamine as claimed in claim 15 exhibit a burst release of berbamine during the initial 2 hours, followed by a controlled release of berbamine for up to 48 hours following administration.

* * * * *